(12) United States Patent
Yadid et al.

(10) Patent No.: US 10,941,386 B2
(45) Date of Patent: Mar. 9, 2021

(54) ENDOINULINASES

(71) Applicant: MIGAL GALILEE RESEARCH INSTITUTE LTD., Kiryat Shmona (IL)

(72) Inventors: Itamar Yadid, Kibbutz Ayelet HaShachar (IL); Rami Cohen, Kibbutz Kfar-Blum (IL); Livnat Afriat-Jurnou, Kibbutz Kfar-Szold (IL)

(73) Assignee: MIGAL GALILEE RESEARCH INSTITUTE LTD., Kiryat Shmona (IL)

( * ) Notice: Subject to any disclaimer, the term of this patent is extended or adjusted under 35 U.S.C. 154(b) by 0 days.

(21) Appl. No.: 16/637,085

(22) PCT Filed: Aug. 7, 2018

(86) PCT No.: PCT/IL2018/050872
§ 371 (c)(1),
(2) Date: Feb. 6, 2020

(87) PCT Pub. No.: WO2019/030755
PCT Pub. Date: Feb. 14, 2019

(65) Prior Publication Data
US 2020/0270592 A1    Aug. 27, 2020

Related U.S. Application Data

(60) Provisional application No. 62/541,820, filed on Aug. 7, 2017.

(51) Int. Cl.
| | |
|---|---|
| *C12N 15/67* | (2006.01) |
| *C12N 9/36* | (2006.01) |
| *C12P 17/00* | (2006.01) |
| *C12N 9/24* | (2006.01) |
| *C12N 15/74* | (2006.01) |

(52) U.S. Cl.
CPC ........... *C12N 9/2402* (2013.01); *C12N 15/74* (2013.01); *C12Y 302/01007* (2013.01)

(58) Field of Classification Search
CPC .............................. C12N 15/52; C12N 9/2431
See application file for complete search history.

(56) References Cited

U.S. PATENT DOCUMENTS

| | | | | |
|---|---|---|---|---|
| 2009/0100536 | A1* | 4/2009 | Adams ................... | A01D 45/00 800/260 |
| 2018/0044687 | A1* | 2/2018 | Thess ..................... | A61K 39/12 |
| 2018/0312545 | A1* | 11/2018 | Baumhof ............. | C07K 14/205 |

OTHER PUBLICATIONS

Naidoo, et al: "Purification and Characterization of an Endoinulinase from Xanthomonas campestris pv. phaseoli KM 24 Mutant", Food Technology and Biotechnology; vol. 53, No. (2), p. 146-153, Feb. 23, 2015.
Onodera, et al: "Molecular Cloning and Nucleotide Sequences of cDNA and Gene Encoding endo-Inulinase from Penicillium purpurogenum", Bioscience, Biotechnology and Biochemistry; vol. 60, No. 11, pp. 1780-1785; Apr. 8, 1994.
Biasini, et al; "Swiss-Model: modelling protein tertiary and quaternary structure using evolutionary information"; Nucleic Acids Research; vol. 42, Apr. 29, 2014.
Chen, et al., "Cloning, Overexpression, and Characterization of a Highly Active Endoinulinase Gene from Aspergillus fumigatus Cl1 for Production of Inulo-Oligosaccharides", Applied Biochemistry and Biotechnology, vol. 175, pp. 1153-1167, 2015.
Chen, et al., "Expression of an endoinulinase from Aspergillus ficuum JNSP5-06 in *Escherichia coli* and its characterization", Carbohydrate Polymers, vol. 88, pp. 748-753, 2012.
Gao, et al, "Characterization of Thermo-stable Endoinulinase from a New Strain Bacillus Smithii T7"; Applied Biochemistry and Biotechnology, vol. 157, pp. 498-506, 2009.
Glibowski, et al, "Amorphous and crystal inulin behavior in a water environment", Carbohydrate Polymers, vol. 83, pp. 635-639, 2011.
Guex, et al., "Automated comparative protein structure modeling with Swiss-Model and Swiss-PdbViewer: A historical perspective", Electrophoresis; vol. 30, pp. S162-S173, 2009.
He, et al., "Enhanced expression of endoinulinase from Aspergillus niger by codon optimization in Pichia pastoris and its application in inulooligosaccharide production", Journal of Industrial Microbiology & Biotechnology, vol. 41, pp. 105-114, 2014.
Liu, et al., "How to achieve high-level expression of microbial enzymes, Strategies and perspectives"; Bioengineered, vol. 4, issue 4, pp. 212-223; Landes Bioscience 2013.
Menzella H.G, "Comparison of two codon optimization strategies to enhance recombinant protein production in *Escherichia coli*", Microbial Cell Factories; vol. 10, No. 15, 2011.
Miller G.L; "Use of Dinitrosalicylic Acid Reagent for Determination of Reducing Sugar"; Analytical Chemistry vol. 31, pp. 426-428, 1959.

(Continued)

*Primary Examiner* — Maryam Monshipouri
(74) *Attorney, Agent, or Firm* — The Roy Gross Law Firm, LLC; Roy Gross

(57) ABSTRACT

A modified endoinulinase is provided, comprising modified wild-type *T. purpuregenus* endoinulinase, or a functional fragment thereof, in which an amino acid residue at each one of one or more positions corresponding to 128, 316, 344, 350 or 504 of wild-type *T. purpuregenus* endoinulinase is substituted, wherein: (i) a tyrosine residue corresponding to Y128 is substituted with H, K or R; a glutamate residue corresponding to E344 is substituted with K, H or R; and a threonine residue corresponding to T504 is substituted with M, S or Y; and optionally an alanine residue corresponding to A316 is substituted with T, S, C or M; (ii) a tyrosine residue corresponding to Y128 is substituted with H, K or R; a glutamate residue corresponding to E344 is substituted with K, H or R; a threonine residue corresponding to T504 is substituted with M, S or Y; and a glutamine residue corresponding to Q350 is substituted with L, G, A, V or I; or (iii) a tyrosine residue corresponding to Y128 is substituted with H, K or R.

20 Claims, 8 Drawing Sheets

Specification includes a Sequence Listing.

(56) References Cited

OTHER PUBLICATIONS

Onodera, et al, "Purification and Substrate Specificity of endo-Typo Inulinase from Penicillium purpurogenum"; Agricultural and Biological Chemistry, vol. 52, pp. 2569-2576, 1988.

Wang, et al, "Efficient Secretory Overexpression of Endoinulinase in *Escherichia coli* and the Production of Inulooligosaccharides", Applied Biochemistry and Biotechnology, vol. 179, pp. 880-894, 2016.

Xu, et al, "Efficient Conversion of Inulin to Inulooligosaccharides through Endoinulinase from Aspergillus niger", Journal of Agricultural and Food Chemistry, vol. 64, pp. 2612-2618, 2016.

Zelena, et al; "*Escherichia coli* as a production host for novel enzymes from basidiomycota"; Biotechnology Advances, vol. 32, pp. 1382-1395, 2014.

Choi, et al, "Secretory and extracellular production of recombinant proteins using *Escherichia coli*"; Applied Microbiology and Biotechnology, vol. 64, pp. 625-635, 2004.

International Search Report, International Application No. PCT/IL2018/050872, dated Nov. 21, 2018.

\* cited by examiner

ENDOINULINASES

CROSS-REFERENCE TO RELATED APPLICATIONS

This application is a National Phase of PCT Patent Application No. PCT/IL2018/050872 having International filing date of Aug. 7, 2018, which claims the benefit of priority of U.S. Provisional Patent Application No. 62/541,820, filed on Aug. 7, 2017. The contents of the above applications are all incorporated by reference as if fully set forth herein in their entirety.

FIELD OF THE INVENTION

The present invention relates in general to improved endoinulinases and their use in hydrolysis of inulin to form fructooligosaccharides.

BACKGROUND OF THE INVENTION

Fructooligosaccharides (FOSs) are naturally occurring fructose polymers that have been shown to provide beneficial health effects as functional food component. FOSs are a type of soluble dietary fibers with low caloric value, has no cariogenic properties, promote the intestinal health by stimulating the growth/activity of beneficial bacteria and support the immune system (Fanaro et al., 2005), A series of clinical studies showed that up to 20 g/day of inulin and/or FOSs is well tolerated (Carabin and Flamm, 1999). The application of FOS with controlled molecular size (degree of polymerization (DP) of 3 to 6) would result in an increased colonic persistence of the prebiotic effect and reduce the risk of chronic disease of distal intestinal region (van de Wiele et al., 2007; Wichienchot et al., 2006). Commercial production of FOS currently rely on the enzymatic hydrolysis of inulin by endo-inulinases from various sources (Chi et al., 2009; Kango and Jain, 2011; Singh et al., 2016). Inulinases are fructofuransyl hydrolases that target the β-2,1 linkage of inulin in an exo or endo fashion to hydrolyze it into fructose, glucose or FOS. Inulinases from different microorganisms have been produced, purified, cloned and characterized. Recombinant inulinases and engineered host strains have many potential industrial applications, however, efficient production processes of highly processive enzymes are required (Wang et al., 2016). Enzymes that are easily produced in high yields usually have low specific activity, such as the endo-imulinase gene product from *Pseudomonas* sp. expressed in *E. coli* (Wang et al., 2016; Xu et al., 2016; Yun et al., 1999). Therefore, there is a need for the combination of high yield production of an inulinase with high specific activity.

SUMMARY OF INVENTION

In one aspect, the present invention provides a modified endoinulinase comprising modified wild-type *T. purpuregenus* endoinulinase, or a functional fragment thereof, in which an amino acid residue at each one of one or more positions corresponding to 128, 316, 344, 350 or 504 of wild-type *T. purpuregenus* endoinulinase is substituted, wherein: (i) a tyrosine residue corresponding to Y128 is substituted with H, K or R; a glutamate residue corresponding to E344 is substituted with K, H or R; a threonine residue corresponding to T504 is substituted with M, S or Y; and optionally an alanine residue corresponding to A316 is substituted with T, S, C or M; (ii) a tyrosine residue corresponding to Y128 is substituted with H, K or R; a glutamate residue corresponding to E344 is substituted with K, H or R; a threonine residue corresponding to T504 is substituted with M, S or Y; and a glutamine residue corresponding to Q350 is substituted with L, G, A, V or I; or (iii) a tyrosine residue corresponding to Y128 is substituted with H, K or R.

In another aspect, the present invention is directed to an isolated nucleic acid molecule comprising a nucleic acid sequence encoding any one of the modified endoinulinases of the present invention or a functional fragment thereof as defined herein.

In an additional aspect, the present invention provides an expression vector comprising any one of the isolated nucleic acid molecules defined herein operably linked to a promoter.

In a further aspect, the present invention is directed to a cell comprising any one of the isolated nucleic acid molecules defined herein or any one of the expression vectors defined herein.

In yet another aspect, the present invention provides a method of producing a modified endoinulinase or functional fragment thereof, the method comprising (i) transfecting a cell with any one of the isolated nucleic acid molecules defined herein or any one of the expression vectors defined herein; and separating said modified endoinulinase from said cell, thereby obtaining a modified endoinulinase or functional fragment thereof.

In still another aspect, the present invention is directed to a method for producing fructooligosaccharides comprising contacting inulin with any one of the modified endoinulinase of the invention.

BRIEF DESCRIPTION OF DRAWINGS

FIGS. 4B-C show a graphs representing the activity of E. coli-expressed protein: (B) To evaluate inulin hydrolysis activity, 10 μl of the soluble cell lysate of each variant was incubated with 1% (w/v) inulin at 55° C. for 30 min and the formation of reducing sugars was evaluated using DNS. (C) Activity in crude lysates was measured using 10 μl of the soluble protein fraction incubated with 1% inulin in Na acetate buffer, pH 5.5 for 20 min at 55° C. and the activity was estimated using the DNS method to quantify the formation of reducing sugars. WT, wild type T. purpuregenus (TP) endoinulinase; R2:1-8G, WT TP endoinulinase with Y128H, E344K and T504M substitutions; R3:5-12G, WT TP endoinulinase with Y128H, A316T, E344K and T504M substitutions.

DETAILED DESCRIPTION OF THE INVENTION

Figure 1:
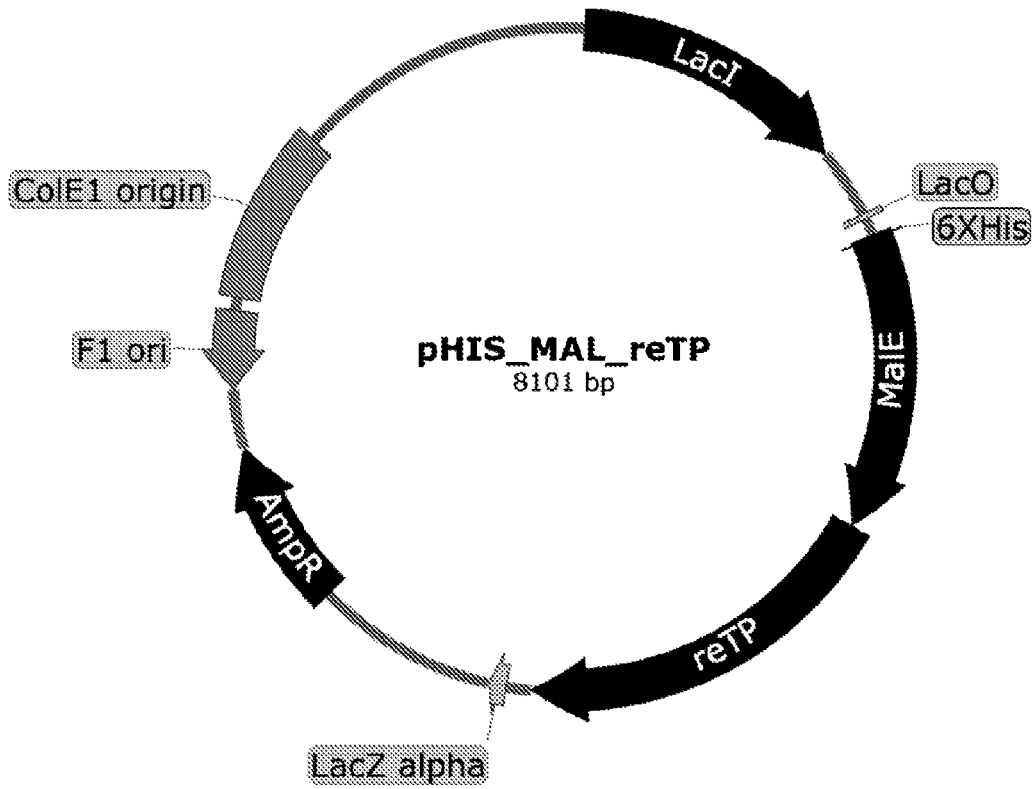
FIG. 1 shows scheme of a plasmid construct (pHIS-MAL-reTP (TP-optimized); 8101 bp) used for the expression of the fungal endoinulinase in *E. coli*. To express the fungal enzyme, a gene encoding the *T. purpuregenus* endoinulinase was codon optimized for expression in *E. coli* and cloned into a modified pMAL vector to result in a fusion protein containing a 6×his tag and a maltose binding protein at the amino terminus. All of the sequence features are derived from the commercial vector pMAL_C2T with the addition of 6 histidine residues (6×His) directly upstream and in frame with the malE gene.

Inulinases are fructofuransyl hydrolases that target the β-2,1 linkage of inulin and hydrolyze it into fructose, glucose and fructooligosaccharides (FOS). Inulinases from different microorganisms have been characterized, purified and produced for industrial applications; however, the high yield production of enzymes with high specific activity is still required to fulfill the growing industrial demand.

Here we used directed enzyme evolution to increase the yield and stability of an endo-inulinase enzyme cloned from the filamentous fungi Talaromyces purpureogenus (Penicillium purpureogenum, ATCC4713), the amino acid sequence of which is as set forth in SEQ ID NO: 1.

A gene encoding the T. purpureogenus endoinulinase lacking its 25 amino acid long signal peptide (Onodera et al., 1996) was first codon-optimized for expression in E. coli. The optimized gene is denoted herein as reTP (recombinant endoinulinase from T. purpureogenus) and its nucleotide sequence is as set forth in SEQ ID NO: 2. The amino acid sequence of the wild-type T. purpureogenus endoinulinase lacking its 25 amino acid long signal peptide is set forth in SEQ ID NO: 3.

To improve the functional yield and the catalytic properties of reTP, a random genetic library was constructed. Thus, four different improved T. purpureogenus inulinase variants were found by the inventors, in all of which a tyrosine residue corresponding to Y128 is substituted with histidine (Y128H). In three variants two additional mutations are found: a glutamate residue corresponding to E344 is substituted with lysine (E344K) and a threonine residue corresponding to T504 is substituted with methionine (T504M). In one variant, a fourth mutation is added to the three mutations described above, wherein an alanine residue corresponding to A316 is substituted with threonine (A316T), and in another variant a fourth mutation is added to the three mutations described above, wherein a glutamine residue corresponding to Q350 is substituted with leucine (Q350L).

It has thus been found in accordance with the present invention that these mutations introduced into the sequence of wild-type T. purpuregenus endoinulinase improves several properties of the enzyme. For example, a clear increase in soluble protein expression was achieved, from <20% solubility in the recombinant wild-type T. purpuregenus endoinulinase (reTP) to approximately 80% in one of the variants. In addition, variants demonstrated an up to 5-fold improvement in hydrolysis activity in cell lysates compared to reTP, as compared with unmodified wild-type T. purpuregenus endoinulinase. Furthermore, variants exhibited altered pH optimum above pH 5, such as pH 5.4, which provides reduced spontaneous uncontrolled inulin degradation during the enzymatic reaction, which occurs preferentially at pH<5 and at temperatures exceeding 60° C.

It was further found in accordance with the present invention that E. coli bacteria expressing the codon-optimized gene encoding for wild type T. purpuregenus endoinulinase having the nucleotide sequence set forth in SEQ ID NO: 2, produce wild-type *T. purpuregenus* endoinulinase having functional activity which is approximately 5-fold higher than the activity previously reported for the enzyme purified from *P. purpurogenum*. The term "functional activity" as used herein refers to the activity of the enzyme as measured in a crude extract, e.g. in terms of units or concentration of substrate hydrolyzed/second (or units or concentration of product formed/second).

The catalytic values and the high yields of the evolved variants are superior to any commercially available enzyme.

It is highly likely that substitutions at these positions of the mutant proteins or functional fragment thereof with an amino acid residue belonging to the same class of amino acids, i.e. a conservative substitution, would result in new mutants having the same properties as the original mutants identified above.

The location of a certain amino acid residue in the proteins or fragments thereof disclosed herein is according to the numbering of the wild type *T. purpureogenus* inulinase as depicted in SEQ ID NO: 1 and is designated by referring to the one-letter code of the amino acid residue and its position in the wild type *T. purpureogenus* inulinase. Thus, for example, the tyrosine at the position corresponding to position 128 of the wild-type *T. purpureogenus* inulinase, also referred to herein as Y128, would be referred to as Y128 also in an inulinase fragment or in a homologous inulinase of a different size according to alignment algorithms well known in the art of protein chemistry, such as (MUSCLE (MUltiple Sequence Comparison by Log-Expectation) or MAFFT (Multiple Alignment using Fast Fourier Transform).

A substitution of an amino acid residue at a certain position with another amino acid residue is designated by referring to the one-letter code of the amino acid residue, its position as defined above and the one-letter code of the amino acid residue replacing the original amino acid residue. Thus, for example, a substitution of Y128 with histidine would be designated Y128H.

Methods for growing bacterial cells and for harvesting secreted proteins from the cells are well-known in the arts (Choi and Lee, 2004). As an unlimiting example, *E. coli* cells may be grown in a suitable growth medium, such as Lysogeny Broth (LB) medium comprising glucose. The bacteria is then harvested and lysed in a suitable lysis buffer and disrupted, for example by sonication. The secreted protein is then isolated and purified from a clarified lysate. In case the protein of interest is tagged for the purpose of facilitating isolation, it is purified on a column that specifically binds the tag, washed and eluted. For example, clarified lysate containing a recombinant protein comprising the protein of interest and a maltose-binding protein is loaded onto an amylose column. The recombinant protein is then eluted with maltose-supplemented column buffer. Protein-containing elution fractions are collected, concentrated and optionally fractionized using a size exclusion column.

Methods for assessing the functionality of an inulinase or a fragment thereof are well known in the art. For example, as disclosed herein below in the examples, the activity may be evaluated by quantifying the amount of reducing ends produced by the inulinase or a fragment thereof using the 3,5-dinitrosalicylic acid (DNS) assay ($\varepsilon$=45 OD/M). An inulinase variant or a fragment with a specific activity, functional expression, yield and/or stability similar or equal to—or better than—that of wild-type inulinase would be considered as a functional inulinase variant or fragment thereof.

Thus, in one aspect, the present invention provides a modified endoinulinase comprising modified wild-type *T. purpuregenus* endoinulinase, or a functional fragment thereof, in which an amino acid residue at each one of one or more positions corresponding to position 128, 316, 344, 350 or 504 of wild-type *T. purpuregenus* endoinulinase is substituted, wherein: (i) a tyrosine residue corresponding to Y128 is substituted with H, K or R; a glutamate residue corresponding to E344 is substituted with K, H or R; and a threonine residue corresponding to T504 is substituted with M, S or Y; and optionally an alanine residue corresponding to A316 is substituted with T, S, C or M; (ii) a tyrosine residue corresponding to Y128 is substituted with H, K or R; a glutamate residue corresponding to E344 is substituted with K, H or R; a threonine residue corresponding to T504 is substituted with M, S or Y; and a glutamine residue corresponding to Q350 is substituted with L, G, A, V or I; or (iii) a tyrosine residue corresponding to Y128 is substituted with H, K or R.

In certain embodiments the modified endoinulinase or functional fragment thereof has improved functional activity or solubility as compared with reTP endoinulinase, or altered pH optimum from about pH 5 of the unmodified wild type *T. purpuregenus* endoinulinase to above pH 5 of the reTP.

In particular embodiments, the improved activity is up to fivefold improvement in hydrolysis activity in cell lysates compared to reTP as measured in a lysate of the bacteria expressing the enzyme; for example, the functional activity of the modified endoinulinase is between about 15-20 µM/s as compared with about 5 µM/s for reTP.

In particular embodiments, the improved solubility of the modified endoinulinase or functional fragment thereof is the presence of more than 50%, 60%, 70%, 80%, 90%, 95% or 99% of the activity, e.g. 80%, in a soluble fraction of lysed bacteria, as shown by an increase in soluble protein expression from <20% solubility in the reTP to approximately 80% in one of the mutants named R3:5-12G (Y128H, A316T, E344K, and T504M).

In particular embodiments, the pH optimum is shifted to a range between pH 5.1 to pH 6, for example pH 5.4.

In certain embodiments, (i) the tyrosine residue corresponding to Y128 is substituted with H (Y128H); (ii) the glutamate residue corresponding to E344 is substituted with K (E344K); (iii) the threonine residue corresponding to T504 is substituted with M (T504M); and (iv) the alanine residue corresponding to A316 is substituted with T (A316T).

Thus, in particular embodiments the modified endoinulinase comprises modified wild-type *T. purpuregenus* endoinulinase, or a functional fragment thereof, in which the following substitutions have been made: (a) Y128H; (b) Y128H, E344K and T504M; (c) Y128J, E344K, T504M and Q350L; or (d) Y128J, E344K, T504M and A316T.

In certain embodiments, the modified endoinulinase or functional fragment thereof as defined in any one of the above embodiments has an amino acid sequence, not including the signal peptide, which is at least 80, 85, 90, 95, 96, 97, 98, or 99% identical to the sequence of wild-type *T. purpuregenus* endoinulinase of SEQ ID NO: 3.

Alternatively, the modified endoinulinase or functional fragment thereof as defined in any one of the above embodiments has no other modifications made to the amino acid sequence of the wild-type *T. purpuregenus* endoinulinase of SEQ ID NO: 3.

For practical purposes, the endoinulinase may be provided as a fusion protein containing a tag useful for separating it from the cell extract by specific binding to a ligand-containing substrate or for improving solubility. For example, any one of the improved endoinulinases of the present invention may be provided as a fusion protein with a 6×his tag and/or a maltose binding protein at the amino terminus.

In another aspect, the present invention is directed to an isolated nucleic acid molecule comprising a nucleic acid sequence encoding any one of the modified endoinulinases of the present invention or a functional fragment thereof as defined herein above.

In certain embodiments, the isolated nucleic acid molecule is optimized for expression in E. coli. Methods for optimizing expression of foreign DNA in E. coli cells are well known in the art e.g. (Burgess-Brown et al., 2008).

In certain embodiments, the isolated nucleic acid molecule encodes for a fusion protein containing a tag useful for separating it from the cell extract by specific binding to a ligand-containing substrate. For example, the nucleic acid sequence encoding any one of the improved endoinulinases of the present invention may be fused to sequences encoding a 6×his tag and/or a maltose binding protein (for example as set forth in SEQ ID NO: 4).

In particular, the isolated nucleic acid molecule comprises a nucleic acid sequence as set forth in SEQ ID NO: 5, SEQ ID NO: 6, SEQ ID NO: 7 or SEQ ID NO: 8, encoding for the improved T. purpuregenus endoinulinase variant (a), (b) (c) and (d) described above, respectively.

Furthermore, the present invention is directed to an isolated nucleic acid molecule comprising a nucleic acid sequence codon-optimized for expression in E. coli, wherein said nucleic acid sequence is as set forth in SEQ ID NO: 2 encoding wild-type T. purpuregenus endoinulinase (reTP).

In an additional aspect, the present invention provides an expression vector comprising any one of the isolated nucleic acid molecules defined herein above operably linked to a promoter.

In a further aspect, the present invention is directed to a cell comprising any one of the isolated nucleic acid molecules defined herein above or any one of the expression vectors defined herein above.

In certain embodiments, the cell is selected from a bacterial, fungal, mammal or plant cell, such as an E. coli cell.

In yet another aspect, the present invention provides a method of producing a modified endoinulinase or functional fragment thereof, the method comprising (i) cultivating a cell defined herein above; and separating said modified endoinulinase from said cell, thereby obtaining a modified endoinulinase or functional fragment thereof.

The cell used in the method may be a cell selected from a bacterial, fungal, mammal or plant cell, such as an E. coli cell.

In certain embodiments, more than 50%, 60%, 70%, 80%, 90%, 95% or 99% of the activity, e.g. 80%, of the modified endoinulinase or functional fragment thereof obtained by the method of the present invention is in a soluble fraction, and its specific activity is about five-fold higher, as compared with unmodified endoinulinase.

In certain embodiments, the modified endoinulinase expressed in the method is T. purpuregenus endoinulinase, in which (i) Y128H; (ii) Y128H, E344K and T504M; (iii) Y128J, E344K, T504M and Q350L; or (iv) Y128J, E344K, T504M and A316T. In certain embodiments, the modified endoinulinase or functional fragment thereof obtained by the method of the present invention as defined in any one of the above embodiments has an amino acid sequence which is at least 80, 85, 90, 95, 96, 97, 98, or 99% identical to the sequence of wild-type T. purpuregenus endoinulinase of SEQ ID NO: 1. In particular, no other modifications are made to the amino acid sequence as compared with the wild-type T. purpuregenus endoinulinase.

Methods for separating, isolating and enriching proteins expressed in isolated cells, such as E. coli cells are well known in the art. For example, the modified endoinulinase may be expressed as a fusion protein having a 6×his tag and/or a maltose binding protein and separated on a Ni-containing and/or maltose containing column (Uhlen, 2008).

In still another aspect, the present invention is directed to a method for producing fructooligosaccharides comprising contacting inulin with any one of the modified endoinulinase of the invention as defined herein above.

In certain embodiments, the modified endoinulinase used in the method is T. purpuregenus endoinulinase, in which (i) Y128H; (ii) Y128H, E344K and T504M; (iii) Y128J, E344K, T504M and Q350L; or (iv) Y128J, E344K, T504M and A316T.

In certain embodiments, the method is for producing fructooligosaccharides with extended product distribution as compared with distribution of fructooligosaccharides obtained using unmodified wild-type T. purpuregenus endoinulinase, such as a mixture of IOS with a DP ranging between DP3 and DP6, or DP2-8 using the R3:5-12G.

The proteins encoded by the nucleic acid molecules of the invention are not limited to those defined herein by specific amino acid sequences but may also be variants of these proteins or have amino acid sequences that are substantially identical to those disclosed above. A "substantially identical" amino acid sequence as used herein refers to a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid with another of the same class, e.g., substitution of one hydrophobic amino acid with another hydrophobic amino acid, a polar amino acid with another polar amino acid, a basic amino acid with another basic amino acid and an acidic amino acid with another acidic amino acid. One or more amino acids can be deleted from the peptide, thus obtaining a fragment thereof without significantly altering its biological activity.

The term "variant" as used herein refers to polynucleotides or polypeptides modified at one or more base pairs, codons, introns, exons, or amino acid residues, respectively, yet still retain the biological activity of a polypeptide of the naturally occurring sequence.

The present invention further relates to an isolated nucleic acid molecule comprising a polynucleotide sequence encoding a protein variant that has an amino acid sequence that is at least 80%, at least 85%, at least 90%, or at least 95, 96, 97, 98, or 99% identical to the amino acid sequence encoded by one of the DNA sequences of SEQ ID NO:4 or SEQ ID NO: 8 as long as each protein variant has equal or substantially similar activity to the protein to which it is similar.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

The term "about" as used herein means that values of 10% or less above or below the indicated values are also included.

The invention will now be illustrated by the following non-limiting examples.

EXAMPLES

Material and Methods
Reagents

Inulin from dahlia tubers (average degree of polymerization 10 (DP-10)), fructose, glucose and sucrose were purchased from Sigma-Aldrich (St Louis, Mo., USA). Fructo-oligosaccharides (FOS) with DP between 3-7 were purchased from Elictyl (Crolles, France). Acetonitrile for HPLC was purchased from J. T. Baker (Avantor, Center Valley, Pa., USA). Double-distilled water (DDW) for HPLC was prepared on an Arium® Pro ultrapure water systems (Sartorius, Goettingen, Germany). Nitrogen gas 99.999% was acquired from Oxygen & Argon Works Ltd (Caesarea, Israel). All other chemicals were of analytical grade.

Gene Cloning

A gene encoding the endo-inulinase from TP with the 25 amino acids signal peptide removed (Onodera et al., 1996) was codon optimized for expression in E. coli using the OptimumGene™ algorithm and synthesized by GenScript®. The synthetic gene was cloned into a modified pMAL-c4x (NEB) vector containing an additional 6×his tag upstream to the MBP reading frame using EcoRI and HindIII restriction sites, for expression with a maltose binding protein (MBP) fusion tag resulting in a pMAL_TP vector (FIG. 1). The cloned gene was transformed into E. coli DH5-α cells and the correct sequence was verified by sequencing.

Expression Optimization.

pMAL_TP was transformed into E. coli BL21 cells and plated on LB agar plates supplemented with 100 µg/ml ampicillin and 1% glucose. A single colony was used to inoculate 3 ml of LB containing 100 µg/ml ampicillin and 1% glucose. The overnight culture was used as a starter for protein expression. Expression conditions: fresh terrific broth (TB) supplemented with 100 µg/ml ampicillin was inoculated 1:100 with the overnight culture and grown at 25, 30 or 37° C. until $OD_{600}$~0.6. Enzyme over-expression was induced by adding IPTG to a final concentration of 0.4 mM and cultures at 25, 30 or 37° C. were shaken at 250 RPM for 40, 24 or 4 h respectively. Cells were harvested by centrifugation, resuspended in lysis buffer (50 mM NaOAc pH 5.4, 300 mM NaCl, 100 µg/mL lysozyme, 0.5 unit/mL DNase, 0.1% tritonX-100, 1:500 protease inhibitor cocktail (sigma P8849) and shaken for 1 h at 950 rpm at room temperature. After centrifugation, the clarified cell lysate was used for activity test and analysis by SDS-PAGE. The best expression conditions were growth at 37° C., following the lowering of the temperature to 20° C. before adding of IPTG.

Expression and Purification of the Optimized TP Gene and its Evolved Variants.

Figure 2A:
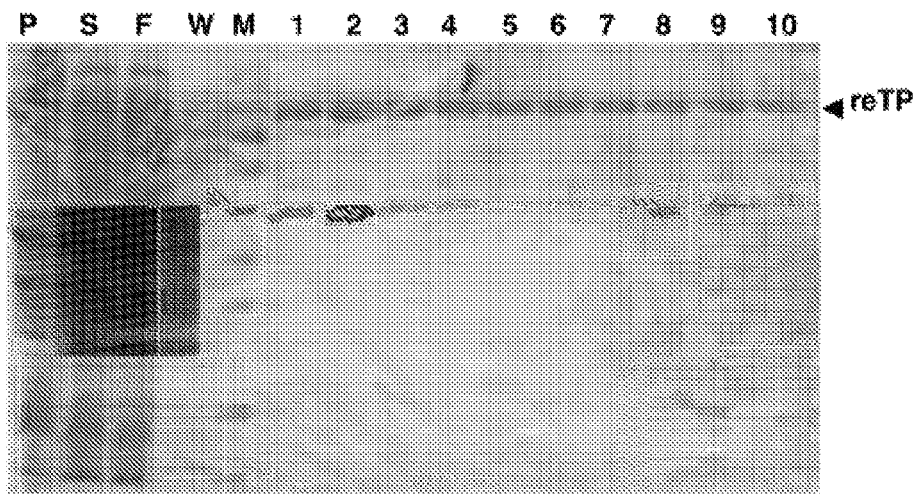
FIGS. 2A-C show expression, purification and activity of the recombinant enzymes. (A) An SDS-PAGE analysis of the expression and amylose column purification procedure. P-insoluble fraction. S-soluble fraction. F-Flow through. W-Wash. M-molecular marker. 1-10 elution fractions after the addition of 10 mM maltose. TP-*T. purpuregenus* endoinulinase. (B) SDS-PAGE analysis of the purification process of reTP variants R3:5-12G after expression in *E. coli*. (1) protein size marker (from the top (kD) 180, 140, 100, 75, 60, 45, 35, 25, 20). (2) crude soluble cell lysate. (3) purified endoinulinase eluted from an amylose column. (4) pooled active fractions eluted from a superdex 200 gel filtration column. Arrow, expected Mw of reTP variant R3:5-12G, WT TP endoinulinase with Y128H, A316T, E344K and T504M substitutions. (C). Inulin hydrolysis activity of the purified enzyme, as determined using DNS, at 55° C., with 27 nM reTP at the indicated substrate concentrations, $K_M=0.78\pm0.14$ mM ($4\pm0.39$ mg/ml), $k_{cat}=850\pm52$ s$^{-1}$, $k_{cat}/K_M=1.15*10^6$.
Figure 2B:
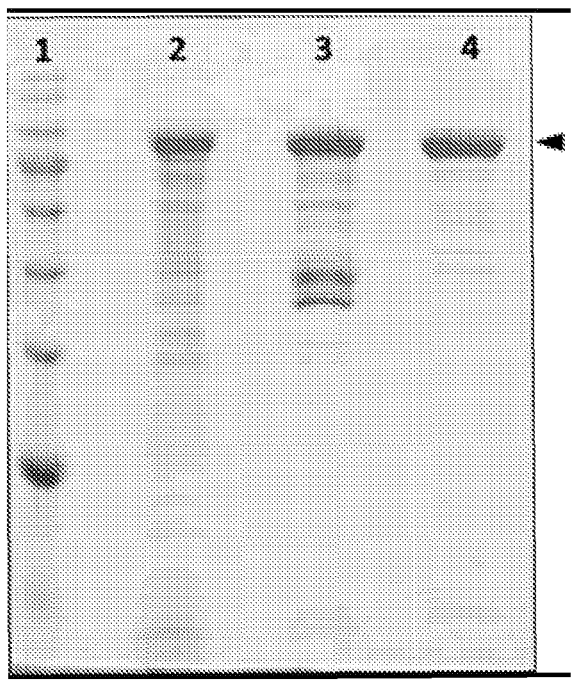

LB medium (5 ml) containing 100 µg/ml ampicillin and 1% (w/v) glucose was inoculated with a single colony of E. coli BL21 cells harboring pMAL_reTP and cultures were grown overnight at 37° C. The next day the culture was used to inoculate 500 ml of fresh TB supplemented with 200 µg/mL ampicillin and 1 mM $MgSO_4$, and the culture was grown at 30° C. until $OD_{600}$~1.2. The temperature was lowered to 20° C. and enzyme expression was induced by adding IPTG to a final concentration of 0.4 mM and the culture was grown with shaking at 250 RPM for 40 h. Cells were harvested by centrifugation, resuspended in the corresponding lysis buffer (50 mM NaOAc pH 5.4, 300 mM NaCl, 100 µg/mL lysozyme, 0.5 unit/mL DNase, 0.1% tritonX-100, 1:500 protease inhibitor cocktail (Sigma-Aldrich, St Louis, Mo., USA, P8849) and disrupted by sonication. The clarified lysate was loaded onto an amylose column (NEB) equilibrated with column buffer (50 mM NaOAc pH 5.4, 150 mM NaCl). The fusion protein was eluted with maltose (10 mM) supplemented column buffer (FIG. 2A). Protein containing elution fractions were collected, concentrated and loaded on a Superdex-200 (GE, GE Healthcare Bio-Sciences, Pittsburgh, Pa., USA) column pre-equilibrated with column buffer. Active fractions were pooled and used for activity tests (FIG. 2B). All purification steps were performed at room temperature, except the size exclusion step that was performed at 4° C. The purity of the fusion enzymes and their concentrations were validated by 12% SDS-PAGE and $OD_{280}$ respectively.

Enzyme Kinetics

Enzyme reactions were carried out using various substrate concentrations (inulin from dahlia purchased from Sigma-Aldrich (St Louis, Mo., USA, I3754) dissolved in 50 mM sodium acetate pH 5.5 and 150 mM NaCl, with enzyme concentration adjusted to result in a linear production of reducing ends during the incubation period (with mixing) in 96 wells microplates at 55° C. Samples were taken at regular intervals and the reactions were stopped by heating the reaction mixtures at 95° C. The activity of the enzyme was evaluated by quantifying the amount of reducing sugars produced using the DNS assay (ε=45 OD/M). The absorbance was measured at 535 nm using infinite M2000 pro, TECAN plate reader. The endoinulinase reTP and its evolved variants were used to study their kinetic parameters ($K_M$ and $k_{cat}$). For the determination of the reaction rate, different inulin concentrations were used, ranging from 0-45 mM (0-8%). The initial reaction rates were corrected for the background rate of spontaneous hydrolysis in the absence of enzyme. Kinetic parameters were obtained by fitting initial rates directly to the Michaelis-Menten equation [$v_0=k_{cat}[E]_0[S]_0/([S]_0+K_M)$] with GraphPad prism (GraphPad Software, Inc. La Jolla, Calif., USA). Data points and errors were obtained from at least three independent measurements.

Library Construction and Screening

Genetic libraries originating from the optimized endoinulinase gene were constructed using GeneMorph II Random Mutagenesis Kit (Agilent Technologies, La Jolla, Calif., USA) adjusted to produce an average of 2 non-synonymous mutations per gene. The estimated theoretical diversity of the library is ~6.5 $e^{10}$ individual variants based on the following calculation:

$$\binom{N}{m} \times m^{19}$$

where N is the number of amino acids (500), m is the average number of mutations (2) and 19 is the number of possible substitutions for a single amino acid. Following the mutagenic PCR, libraries were cloned back into the modified pMAL vector as described for the pMAL_reTP. The cloned libraries were transformed into BL21 cells and plated on LB plates supplemented with 100 µg/ml ampicillin and 1% (w/v) glucose. In each round of screening, approximately 600 randomly chosen single colonies were picked and grown overnight in 96 deep-well plates containing 500

µl of LB supplemented with 100 µg/mL ampicillin and 1% (w/v) glucose, at 37° C. with shaking. The overnight cultures were used to inoculate (at 1:20 dilution) fresh 500 µl TB supplemented with 200 µg/mL ampicillin in 96 deep-well plates. Cells were grown at 30° C. with shaking for about 4 h, to an $OD_{600}$=0.6-1.0, IPTG was then added (final concentration 0.4 mM) to induce expression of the endoinulinase variants. Following overnight incubation at 20° C., the cells were pelleted and freezed at −80° C. Cells were resuspended in lysis buffer (50 mM NaOAc pH 5.4, 150 mM NaCl, 100 µg/mL lysozyme, 0.5 unit/mL benzonase, 0.1% triton X-100, 1:500 protease inhibitor cocktail for 1 h shaking at 960 RPM at 25° C.). The lysates were clarified by centrifugation, diluted in activity buffer, and assayed for hydrolysis of inulin using the 3,5-dinitrosalcylic acid (DNS) assay (Miller, 1959) One unit of inulinase activity was defined as the quantity of enzyme required to liberate 1 µmol of fructose equivalent from inulin per minute at 55° C., and specific activity was defined as units per mg protein. In each round, variants with top activities were selected to serve as parents for the next round, where their genes were shuffled and mutated using GeneMorphll kit.

pH Optimum and Stability of reTP and its Evolved Variants

The effect of pH on reTP and its evolved variants was evaluated by incubating the enzymes for 1 h at 4° C., with pH solution ranging from 3.5 to 8.2, followed by endoinulinases activity measurements using the DNS assay, in 100 mM potassium phosphate, 150 mM NaCl, pH 5.4 at 55° C. Enzyme concentration was set to be 18.2 ng/µl for reTP, R2:1-8G and R3:5-12G, and 4.5 ng/µl for variant R1:1-7B. 50 mM sodium acetate buffer, with 150 mM NaCl, was used for obtaining pH values 3.5-5.5, while 100 mM potassium phosphate buffer, with 150 mM NaCl was used for pH 5.5-8.2.

Temperature Optimum and Thermostability of Optimized reTP and its Evolved Variants Temperature optimum was measured by performing endoinulinase assay at temperature ranging from 4 to 70° C., 2% (w/v) inulin (dissolved in 50 mM sodium acetate buffer (pH 5.4), 150 mM NaCl), was incubated for 30 min with optimized reTP and its evolved variants. Enzyme concentration was set to be 18.2 ng/µl for reTP, R2:1-8G and R3:5-12G, and 4.5 ng/µl for R1:1-7B. b. Thermal stability was tested by pre-incubating the enzyme variants at temperatures ranging between 4-70° C. for 1 h. Residual activity was than measured by following the thermal activity analysis.

Effects of Metal Ions and Inhibitors on reTP and its Evolved Variants Inulinase Activity The effect of metal ions and inhibitors on the inulinase activity was determined by adding different elements in the concentration of 1 mM (for $K^+$, $Ca^{2+}$, $Mg^{2+}$, $Cu^{2+}$, $Al^{2+}$, $Zn^{2+}$, $Ni^{2+}$, EDTA, DTT, SDS) or 0.1% (w/w) for Triton X-100, to the activity buffer 50 mM sodium acetate buffer (pH 5.4), 150 mM NaCl. With 2% (w/v) inulin, 18.2 ng/µl of reTP and the evolved variants. Results are presented as residual activity compared to the control (no metal/inhibitor added).

Preparation of Fructooligosaccharides Standard Solutions

Mixed standard stock solutions containing inulin-type FOS (DP3-DP7) were prepared in double-distilled water. The concentrations of DP3-DP7 were about 2 mg/mL. The standard stock solutions were stored at 4° C. before use. Working standard solutions were prepared by dilution in 50 mM sodium acetate buffer (pH 5.4), 150 mM NaCl.

TLC Analysis of Hydrolysis Products

The products of inulin hydrolysis by purified endoinulinases were analyzed by thin-layer chromatography (TLC). The enzyme reaction contained purified enzyme (0.25 µM) with 2 or 6% inulin at 50 mM sodium acetate buffer (pH 5.4), 150 mM Nacl, for 1 or 24 h at 48° C. 1 µl of each sample was spotted on TLC plate (Silica gel from Mercury). First running solution: Butanol/Ethanol/DDW (5:5:3, v/v/v) and the second running solution: Acetone/DDW (9:1, v/v). Inulo-oligosacharides were detected using 0.3% (w/v) of N-(1-naphthyl) ethylenediamine and 5% (v/v) sulfuric acid in methanol. Color development was initiated by placing the plates in an oven at 150° C. for about 5 min until bends were observed.

HPLC-CAD Analysis

Chromatographic analysis was performed on an Agilent (Santa Clara, Calif., USA) 1200 Series HPLC system equipped with degasser, pump, auto sampler and column compartment, coupled with Corona charged aerosol detector (CAD) instrument (ESA, Chelmsford, Mass., USA). Data processing was carried out with ChemStation B 04.02 software (Agilent). The $N_2$ pressure of the CAD was adjusted to 35 psi and response range was set to 100 pA. Separations were performed on a Waters XBridge Amide column (4.6× 250 mm; 2.5 µm). The mobile phase was consisted of water (A) and acetonitrile (B) with gradient elution of 75%-45% B at 0-30 min, 45-75% at 30-32 min and equilibrated with 75% B for 10 min. The column temperature was set at 30° C. The flow rate was 1.0 mL/min; injection volume was 10 µL.

3D Homology Modeling of the Endoinulinase from *T. purpureogenus*

The solved structure of homologous endoinulinase from *A. ficcum* (pdb 3RWK, in blue) was used as a template to create a 3D model of endo-inulinase from *T. purpuregenus* using the SWISS-MODEL server (Guex et al., 2009).

Example 1: Expression of WT Inulinase from *T. purpureogenus*

Figure 2C:
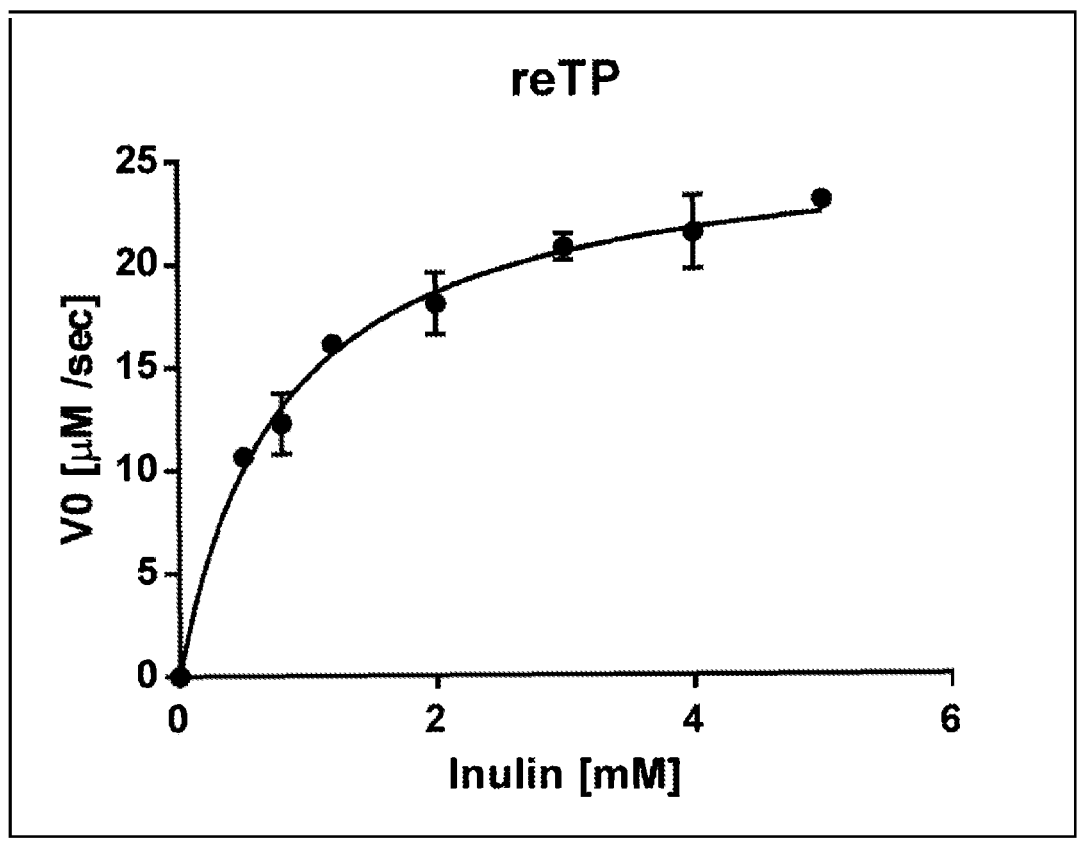

Directed enzyme evolution in *E. coli* cells enables high efficiency transformation, simple host cell handling and the use of a large array of molecular tools. However, most endoinulinases of fungal origin are not well expressed in *E. coli*. Apart from effects such as cellular conditions, molecular chaperons and localization (Liu et al., 2017; Zelena et al., 2014), it has been shown that codon optimization improves the heterologous expression of enzymes and endoinulinases specifically (He et al., 2014; Menzella, 2011). Therefore, a gene encoding the *T. purpureogenus* endoinulinase lacking its 25 amino acids signal peptide (Onodera et al., 1996) was codon-optimized, for expression in *E. coli*, using the OptimumGene™ algorithm and synthesized by GenScript®. The optimized gene is denoted herein as reTP (recombinant endoinulinase from *T. purpureogenus*). The optimized gene was cloned into a pMAL vector (NEB) downstream to the malE open reading frame (ORF), to drive cytoplasmic expression. Fusion of the endoinulinase to the maltose binding protein (MBP) resulting from the in-frame cloning with the malE gene served two purposes: increasing protein solubility and facilitating purification (FIG. 1). The enzyme was then over-expressed in *E. coli*. Following purification (as described in the Material and Methods section), a functional biochemical assay was performed to verify the ability of the purified protein to hydrolyze inulin (using inulin with a DP~10). A Michaelis-Menten plot was generated following a DNS assay (FIG. 2C) and the enzyme's kinetic profile served as a reference for the functionality of the recombinant enzyme. Our heterologous expression system yielded a functional fusion protein with properties similar to that of the endoinulinase previously purified from the fungus *T. purpureogenus* (Onodera and Shiomi, 1988) (annotated here as TPwt) (Table 1) indicating that the fusion protein (MBP) and the host organism had no significant effect on the enzymes kinetic properties.

Figure 3:
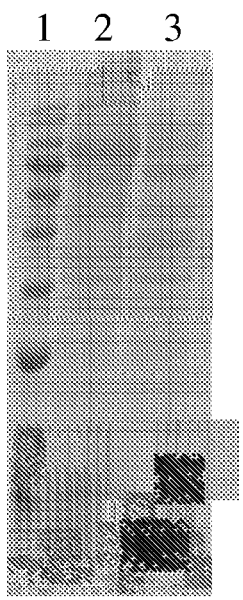
FIG. 3 shows the partitioning of the recombinant enzyme after expression in *E. coli*: SDS-PAGE showing the partitioning of the recombinant enzyme between the soluble and the insoluble fraction after cell lysis. Over 80% of the expressed wt enzyme ended up as inclusion bodies. 1, molecular weight marker; 2, TPwt insoluble fraction; 2, TPwt soluble fraction.

The maximal activity was obtained by inducing protein expression at 30° C. for 40 h, however, over 80% of the expressed protein ended up in the insoluble fraction (FIG. 3).

Example 2. Library Construction and Directed Evolution

To improve the functional yield and the catalytic properties of reTP, a random genetic library was constructed using the GenemorphII kit (Agilent). The mutation rate was calibrated to incorporate ~2 nonsynonymous mutations per gene, thereby creating a library with a theoretical complexity of 6.5 $e^{10}$ (see the Material and Methods section for the calculation). Transformation of the initial library into *E. coli* cells resulted in ~20,000 individual colonies. For each round of screening, 600 randomly chosen colonies were grown and protein expression was induced in 96 deep-well plates. Cells lysates were then incubated with inulin, and assayed for activity using a DNS assay. In each round 10-15 clones exhibiting above 2 folds improvement in activity compared to reTP were selected. Improved variants were streaked on agar plates and expressed in 3 ml cultures in triplicates to validate their improvements, and to evaluate product range by analyzing the reaction products using TLC. Improved variants were therefore selected for higher expression levels, solubility, hydrolysis rates and product range. This procedure was repeated three times with the 3-5 of the best variants from each round serving as starting points for the next round of mutagenesis and screening. The acquired mutations in selected variants from each round are summarized in Table 1.

Figure 4A:
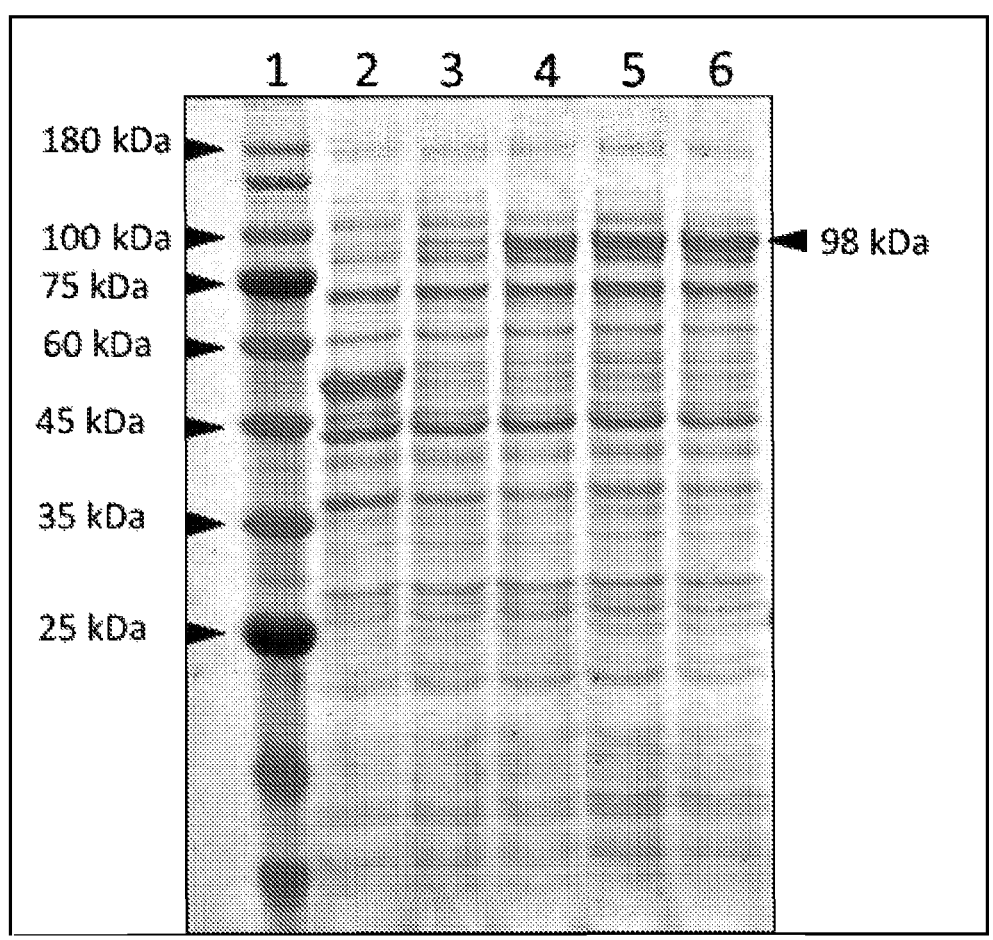
FIGS. 4A-C deptic analysis of wild type and the recombinant endo-inulinase expression and activity. (A) an SDS-PAGE analysis of wt and the recombinant endo-inulinase. Soluble cell lysate after 48 h of expression at 30° C. and analysis by SDS-PAGE indicated the improvement of soluble expression, as evident by the increase in soluble protein expression of the evolved variants compared to reTP. (1) protein size marker (2) cell lysate from cells harboring the empty expression vector. (3) cell lysate from cells expressing reTP (4) cell lysate from cells expressing variant R1:1-7B (Y128H) (5) cell lysate from cells expressing variant R2:1-8G (Y128H, E344K and T504M). (6) cell lysate from cells expressing variant R3:5-12G (Y128H, A316T, E344K and T504M).
Figure 4B:
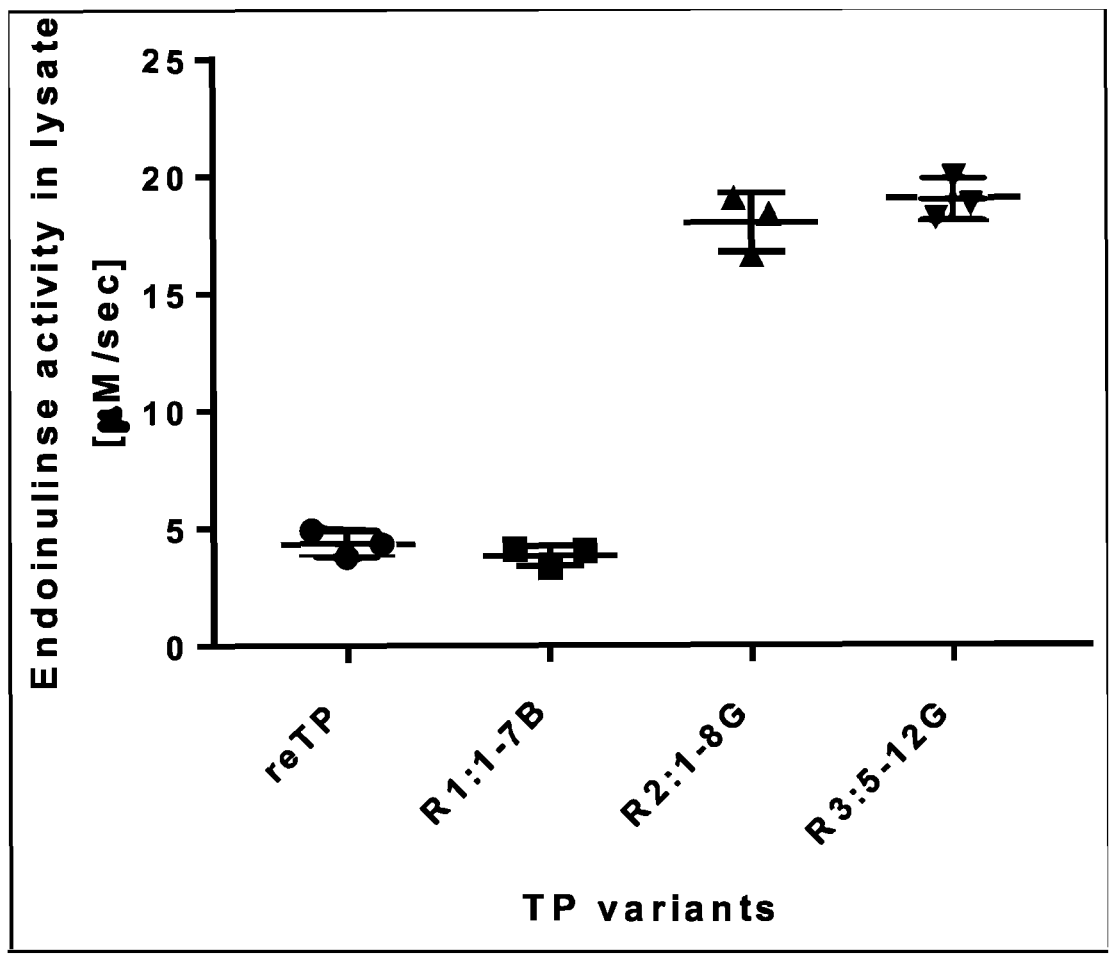

Example 3. Evolved Endoinulinase Variants Exhibit Increased Solubility and Activity Variants from each screening round (R1, R2 and R3) were expressed and their activity and soluble expression were analyzed and compared to reTP, by an inulin hydrolysis assay and SDS-PAGE, respectively. A clear increase in soluble protein expression was achieved, from <20% solubility in the reTP to approximately 80% in R3:5-12G, a variant isolated after the third round of screening (FIG. 4A). In addition, variants R2:1-8G and R3:5-12G demonstrated an up to 5-fold improvement in hydrolysis activity in cell lysates compared to reTP (FIG. 4B).

Figure 4C:
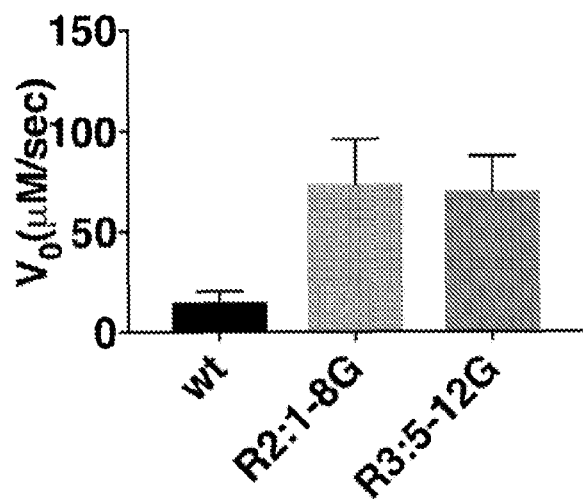

WT and improved variants were expressed in *E. coli* as described in materials and methods and the soluble protein fraction was separated after cell lysis. Equal amount of cell lysate was used to compare between the variants in an assay for inulin degradation. The activity of the evolved variants showed up to 5-fold improvement in functional expression over the WT clone (FIG. 4C).

Example 4: Characterization of the Evolved Variants

In an effort to identify the molecular bases leading for improved solubility and functional activity, the selected variants were subjected to various biochemical characterizations. To this end, the recombinant proteins were purified to near homogeneity, using an amylose affinity chromatography followed by gel filtration, as described in the methods section (FIGS. 2A and B). The inulin hydrolyzing activity of the purified enzymes was then measured. A specific activity of 413 U/mg protein was measured for reTP, which is approximately 5-fold higher than the activity previously reported for the enzyme purified from *P. purpurogenum* (Onodera and Shiomi, 1988). The evolved variants displayed higher $k_{cat}$ values, and variant R1:1-7B exhibited 15-fold increase in $k_{cat}$ compared to that of the TPwt purified from *P. purpurogenum*(Onodera and Shiomi, 1988), and 2-fold higher than reTP, Table 1.

Figure 6A:
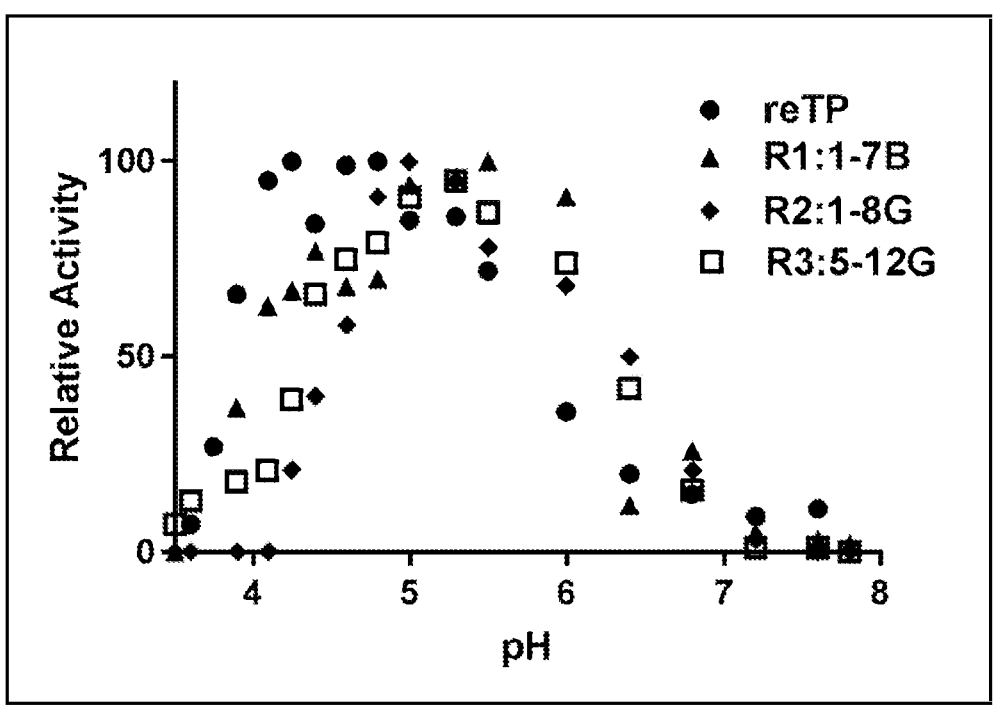
FIGS. 6A-B shows the effect of pH on the activity and stability of reTP and its variants. (A) The optimal pH was determined by measuring enzyme activity over a pH range (3.5-8.2). (B) pH stability was tested by pre-incubating the enzymes without substrate for 1 h at 4° C., in buffers with a range of pH values (3.5-8.2). Residual activity was then measured at the optimal pH and at a set temperature of 55° C.
Figure 6B:
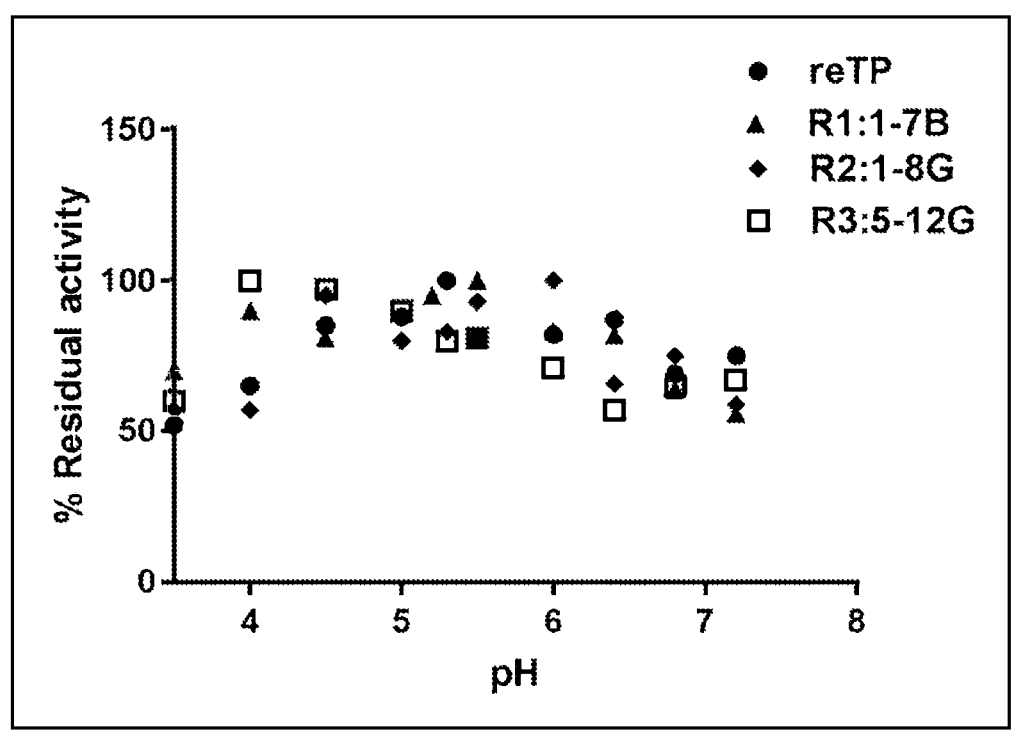

Example 5. Endoinulinase Variants with Altered pH Optimum can be Achieved Using Directed Evolution The pH optimum of most of the characterized inulinases is acidic, as in the case of the *A. awamori* inulinase (pH 4.5) (Arand and Golubev 2002) and the *A. ficcum* inulinase (pH 5.0)(Chen et al., 2012). A similar pH optimum was observed for reTP (FIG. 6A). However, inulin is degraded spontaneously at pH<5 and at temperatures exceeding 60° C. (Glibowski and Pikus, 2011). To reduce spontaneous uncontrolled inulin degradation during the enzymatic reaction, we aimed to increase the enzyme's optimal pH for activity. Hence, we set the pH during the screening process to 5.4, where less spontaneous hydrolysis occurs, and the reTP enzyme exhibit 80% of its maximal activity. As FIG. 3a indicates, the pH optimum of the evolved variants shifted to 5.4 in response to the selection pressure. The pH stability of the variants was tested as well, and showed similar activity profiles to the optimized reTP (FIG. 6B). These results indicate that variants with specific properties can be easily selected by setting the appropriate screening conditions, leading the way for the selection of tailor-made enzymes for specific and favorable reaction conditions.

Figure 7A:
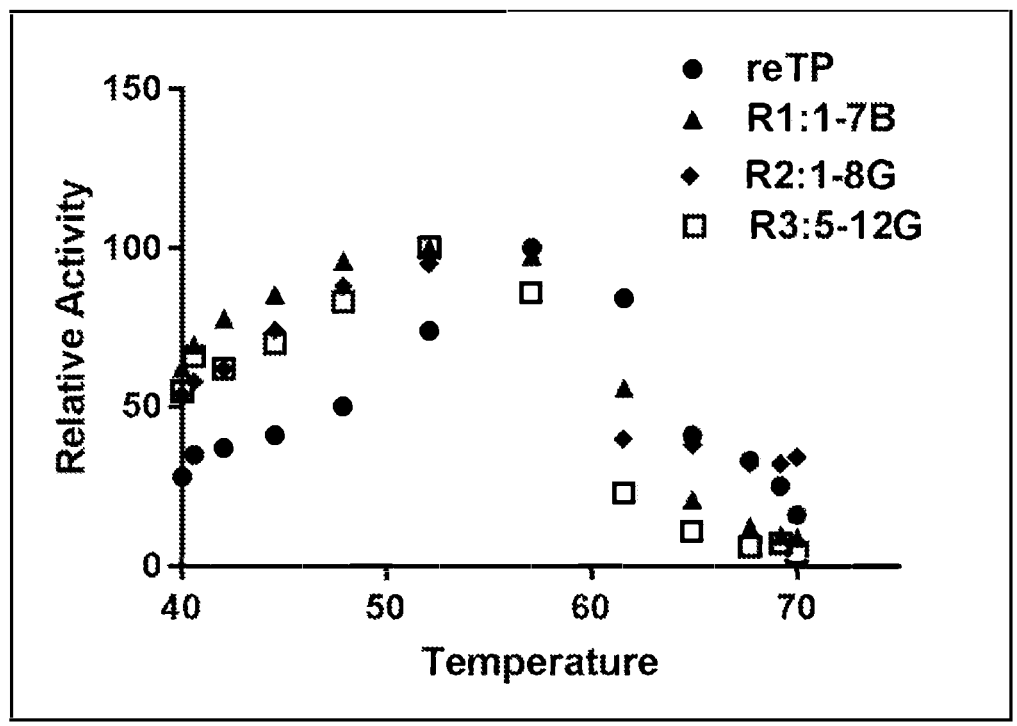
FIGS. 7A-B shows the effect of temperature on the activity and the stability of reTP and its evolved variants. (A) Temperature optimum was determined by measuring inulin enzymatic hydrolysis rates over a temperature range of 4-70° C. (B) Thermal stability was tested by pre-incubating the enzymes without substrate for 1 h at the designated temperature (4-70° C.). Residual activity was then measured at the optimal pH and at a set temperature of 55° C.
Figure 7B:
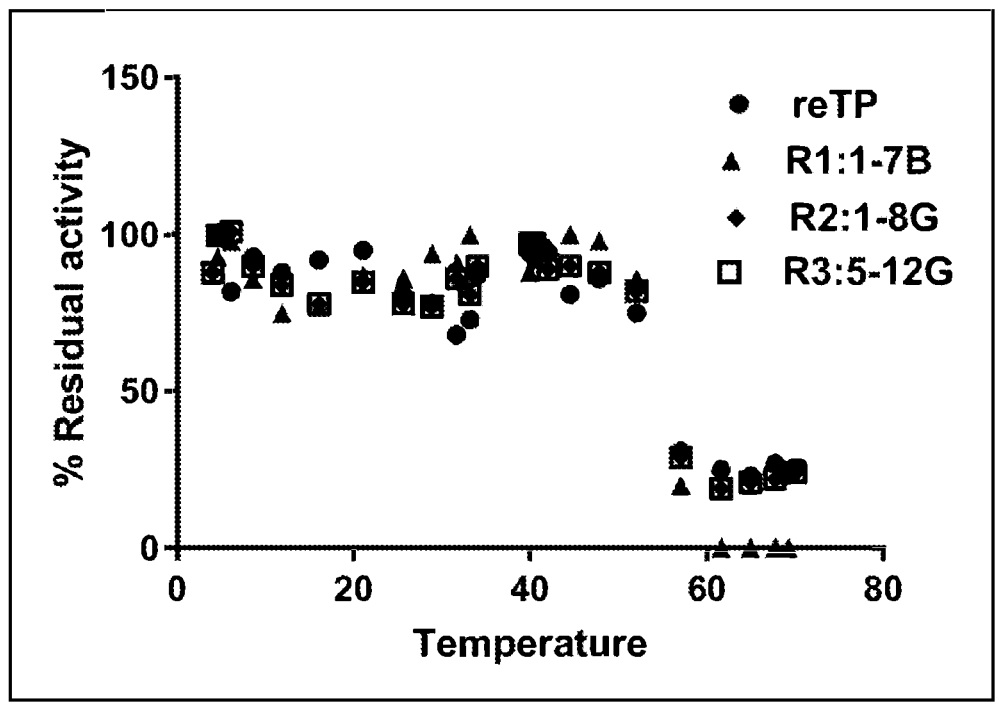

The optimal temperature of reTP and its evolved variants was 55° C., which is in agreement with those reported for other microbial inulinases (Xu et al., 2016) (FIG. 7A). In addition, both reTP and its variants demonstrated thermal stability, with >80% residual activity when incubated at temperatures up to 50° C. (FIG. 7B). This finding is in agreement with the thermal stability reported for the enzyme purified from *T. purpureogenus*(Onodera and Shiomi, 1988).

Figure 8:
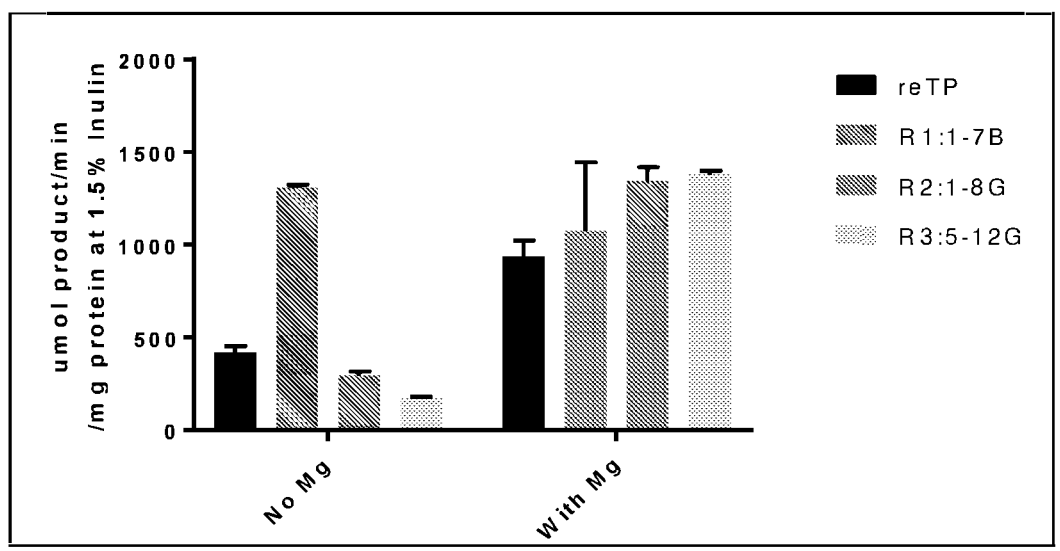
FIG. 8 shows increased enzyme activity upon addition of $Mg^{+2}$. The effect of $Mg^{+2}$ on the inulinase activity was determined by expressing and purifying the endoinulinase variants with and without the addition of $Mg^{2+}$; after purification, enzymatic activity was measured in the presence of 1.5% (w/v) inulin.

Example 6. Addition of $Mg^{2+}$ Ions is Required to Maintain High Activity of Variants from Advanced Rounds of Evolution The effect of different additives on enzyme's activity was tested by supplementing purified enzyme before the addition of inulin with the following: $K^+$, $Ca^{2+}$, $Mg^{2+}$, $Al^{2+}$, $Cu^{2+}$, $Zn^{2+}$, $Ni^{2+}$, EDTA, DTT at 1 mM concentration, and SDS or Triton X-100 at 0.1% (v/v). The addition of EDTA decreased the activity of reTP, R2:1-8G and R3:5-12G by 70%, 82% and 50%, respectively (Table 2). In accordance, the addition of metal ions and $Mg^{2+}$ in particular, increased the inulinase activity. In the presence of $Mg^{2+}$, the relative activity of reTP, R2:1-8G and R3:5-12G increased to 136%, 210% and 198%, respectively, as compared to the reactions without the additions of the metal ion (Table 2). These results suggest that the activity of the evolved variants became more dependent on the presence of metal ions than that of the reTP, especially after rounds #2 and #3. To further test this, we included $Mg^{2+}$ in the growth medium used for protein expression and in the buffers used for protein purification, and compared the activity of the enzymes that were expressed and purified with and without the addition of $Mg^{2+}$. As seen in FIG. 8, the activity of reTP increased by 2-fold, of R2:1-8G by 4.5-fold and of R3:5-12G by 8-fold. Moreover, the specific activity of R3:5-12G in the presence of $Mg^{2+}$ reached a value of 1380 U/mg, which is higher than that of most endoinulinases described in the literature. For example, *A. ficuum* endoinulinase expressed and purified from *E. coli* exhibited a specific activity of 75.22 U/mg (Wang et al., 2016), the *Bacilus smithii* T7 endoinulinase had a reported specific activity of 833 U/mg (Gao et al., 2009) and the *Xanthomonas campestris* pv. *phaseoli* KM 24 mutant endoinulinase showed a specific activity of 119 U/mg (Naidoo et al., 2015). Recently, expression of the *A. fumigatus* C11 endoinulinase in *E. coli* using high cell-density fermentation, yielded an enzyme with specific activity similar to that of our evolved variants (1590 U/mg)(Chen et al., 2015).

Figure 5:
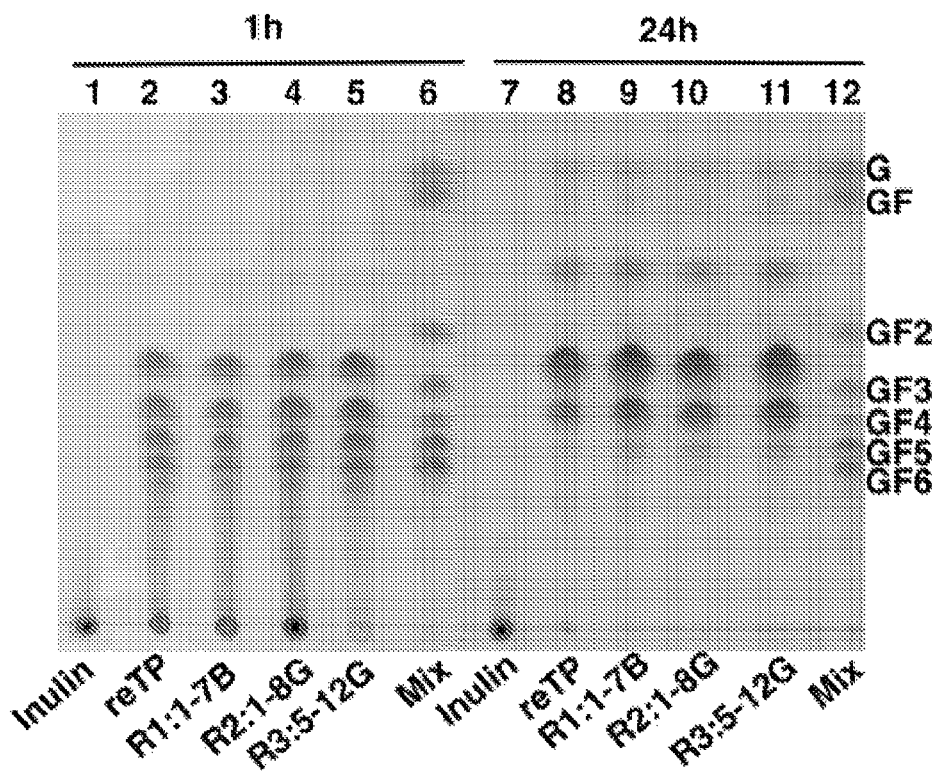
FIG. 5 shows TLC assays comparing inulin hydrolysis products generated by reTP and its evolved variants. (A). Samples were tested after 1 h and after 24 h of incubation with 6% inulin as substrate. Lanes 1: no enzyme, lanes 2: reTP and lanes 3, 4, 5: reactions with the evolved variants. Lanes 6: FOS standards mixture: Fructose, Sucrose, GF2, GF3, GF4, GF5 and GF6. Lane 7: reaction with no enzyme added, after a 24 h incubation. Lane 8: reaction with the optimized reTP endoinulinase, after a 24 h incubation. Lanes 9-11: reaction with the evolved variants after a 24 h incubation: Lane 9: R1:1-7B-11 (Y128H). Lane 10: (R2:1-8G (Y128H, E344K and T504M). Lane 11: R3:5-12G (Y128H, A316T, E344K and T504M). Lanes 12: Standards mixture.

Example 7. Analysis of IOS Distribution Resulting from Inulin Hydrolysis Using the Evolved Variants TLC and HPLC were used to characterize the distribution of products resulting from inulin hydrolysis by the purified reTP and its evolved variants. The ability of the methods to detect the reaction product were validated using inulin and inulin type FOS ranging from DP2-6 (FIGS. 5A-B). As expected, both methods indicated that IOS were the predominant end products of the hydrolysis; HPLC analysis indicated that ~91% of the products are IOS (not shown). Upon the use of 2% (w/v) inulin as substrate in the reaction mixture, a mixture of IOS with a DP ranging between DP2 and DP6 was obtained after 1 h incubation, while after 24 h of incubation, the main product was mostly DP3 (FIG. 5a). When a higher inulin concentration was used (6%), a broader product distribution was observed and even after incubation for 24 h, the products ranged between DP2-8 (FIG. 5b). TLC results indicated that only variant R3:5-12G was able to fully consume the high concentration (6%) of inulin (FIG. 5b).

Example 8. Analysis of Mutations Accumulated During the Evolution Process

Figure 9:
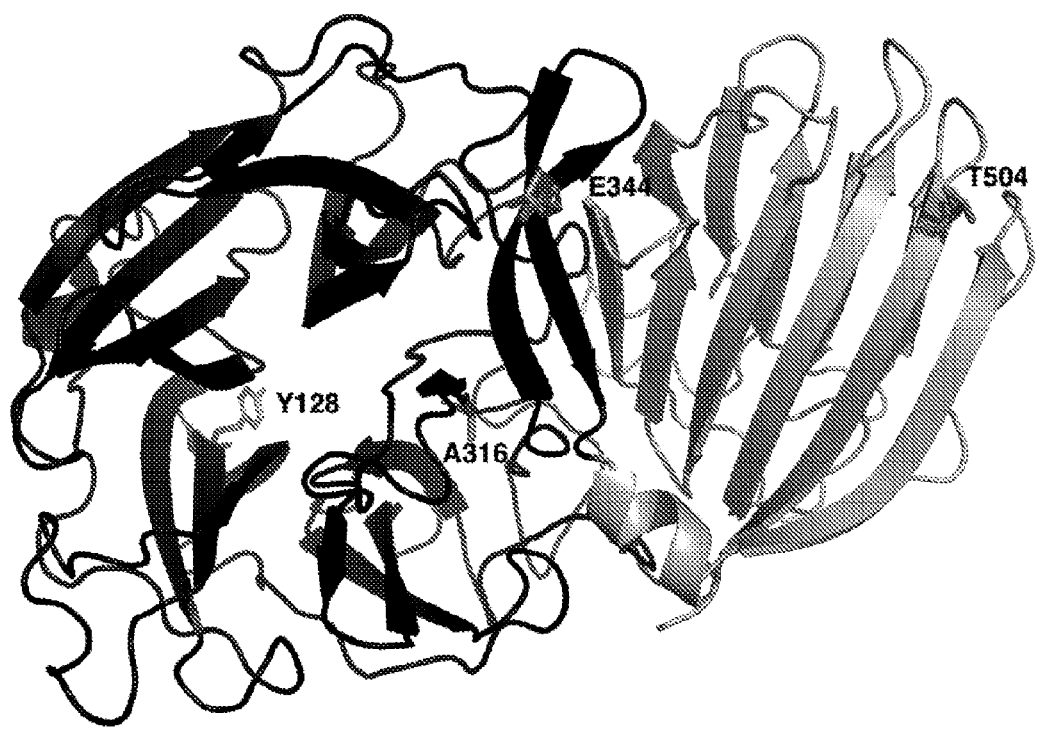
FIG. 9 shows a structure homology model of endo-inulinase from T. purpuregenus. The solved structure of homologous endo-inulinase from A. ficuum (pdb 3RWK, in blue) was used as a template to create a 3D model of endo-inulinase from T. purpuregenus using the SWISS-MODEL server (swissmodel.expasy.org/). The residues that were mutated and fixated in the evolution experiments are labeled; Residues Y128 and A316 are within the active site, while Q350, E344 and T504 are located at the surface.

Understanding the function of mutations selected by directed enzyme evolution can be achieved, in some cases, by phylogenetic and structural analysis. As there is currently no available structure for the *T. purpuregenus* endoinulinase, we used the atomic structure of the homolog from *A. ficcum* endoinulinase (pdb 3RWK, 73% identity) to generate a 3D model using the Swiss-model server (Biasini et al., 2014), (FIG. 9). The reconstructed model indicated that mutation Y128H, which is in close proximity to the active site, had a definite role in the modified enzyme catalytic activity, as it was acquired in the first round, and increased the $k_{cat}$ of R1:1-7B (only mutation) by 2-fold compared to reTP. Since R1:1-7B did not exhibit increased functional expression levels and was least affected by the addition of metal ions (FIGS. 4B and 8), it seems that its selection in the screening process was purely due to its increased catalytic activity.

TABLE 1

Kinetic parameters of TPwt, reTP and the evolved variants (purified from *E. coli.*) and their corresponding mutations.

| Endoinulinase | Mutations | $K_M$ [mM] | $k_{cat}$ [s$^{-1}$] | $k_{cat}/K_M$ [s$^{-1}$/M$^{-1}$] | SEQ ID NO. of encoding DNA[b] |
|---|---|---|---|---|---|
| TPwt[a] | | 0.21 | 120 | 0.57*10$^6$ | |
| reTP (MBP fused) | | 0.78 ± 0.14 | 850 ± 52 | 1.15*10$^6$ | 2 |
| R1: 1-7B (MBP fused) | Y128H | 2.82 ± 0.04 | 1797 ± 97 | 0.64*10$^6$ | 3 |
| R2: 1-8G (MBP fused) | Y128H 344K T504M | 2.40 ± 0.04 | 792 ± 45 | 0.33*10$^6$ | 4 |
| R3: 2-2E (MBP fused) | Y128H E344K Q350L T504M | NA | NA | NA | 5 |
| R3: 5-12G (MBP fused) | Y128H A316T E344K T504M | 3.12 ± 0.38 | 685 ± 31 | 0.2*10$^6$ | 6 |

[a]from(Onodera and Shiomi, 1988)
[b]sequences of reTP not including MBP

TABLE 2

Effect of metal ions and additives on the activity of reTP and its evolved variants.

| Additives | Concentration | reTP | R1: 1-7B | R2: 1-8G | R3: 5-12G |
|---|---|---|---|---|---|
| Control | 1 mM | 100 ± 19 | 100 ± 6 | 100 ± 8 | 100 ± 7 |
| K$^+$ | 1 mM | 98 ± 15 | 109 ± 6 [a] | 111 ± 3 | 91 ± 9 [a] |
| Zn$^{2+}$ | 1 mM | 66 ± 9 [a] | 83 ± 28 | 76 ± 5 [a] | 112 ± 15 |
| Ca$^{2+}$ | 1 mM | 116 ± 6 | 147 ± 9 [a] | 126 ± 1 [a] | 130 ± 24 |
| Ni$^{2+}$ | 1 mM | 86 ± 9 | 96 ± 3 | 111 ± 3 | 133 ± 14 |
| Cu$^{2+}$ | 1 mM | 50 ± 6 [a] | 2 ± 0 [a] | 3 ± 1 [a] | 6 ± 2 [a] |

REFERENCES

Biasini, M., Bienert, S., Waterhouse, A., Arnold, K., Studer, G., Schmidt, T., Kiefer, F., Cassarino, T. G., Bertoni, M., Bordoli, L., et al. (2014). SWISS-MODEL: Modelling protein tertiary and quaternary structure using evolutionary information. Nucleic Acids Res. 42.

Chen, M., Lei, X., Chen, C., Zhang, S., Xie, J., and Wei, D. (2015). Cloning, Overexpression, and Characterization of a Highly Active Endoinulinase Gene from *Aspergillus fumigatus* C11 for Production of Inulo-Oligosaccharides. Appl. Biochem. Biotechnol. 175, 1153-1167.

Chen, X. M., Xu, X. M., Jin, Z. Y., and Chen, H. Q. (2012). Expression of an endoinulinase from *Aspergillus ficuum* JNSP5-06 in *Escherichia coli* and its characterization. Carbohydr. Polym. 88, 748-753.

Choi, J. H., and Lee, S. Y. (2004). Secretory and extracellular production of recombinant proteins using *Escherichia coli*. Appl. Microbial. Biotechnol. 64, 625-635.

Gao, W., Bao, Y., Liu, Y., Zhang, X., Wang, J., and An, L. (2009). Characterization of thermo-stable endoinulinase from a new strain *bacillus smithii* T7. Appl. Biochem. Biotechnol. 157, 498-506.

Glibowski, P., and Pikus, S. (2011). Amorphous and crystal inulin behavior in a water environment. Carbohydr. Polym. 83, 635-639.

Guex, N., Peitsch, M. C., and Schwede, T. (2009). Automated comparative protein structure modeling with SWISS-MODEL and Swiss-PdbViewer: A historical perspective. Electrophoresis 30.

He, M., Wu, D., Wu, J., and Chen, J. (2014). Enhanced expression of endoinulinase from *Aspergillus niger* by codon optimization in *Pichia pastoris* and its application in inulooligosaccharide production. J. Ind. Micro biol. Biotechnol. 41, 105-114.

Liu, L., Yang, H., Shin, H., Chen, R. R., Li, J., Du, G., Chen, J., Liu, L., Yang, H., Shin, H., et al. (2017). How to achieve high-level expression of microbial enzymes How to achieve high-level expression of microbial enzymes Strategies and Perspectives© 2013 Landes Bioscience. Do not distribute. 5979, 212-223.

Menzella, H. G. (2011). Comparison of two codon optimization strategies to enhance recombinant protein production in *Escherichia coli*. Microb. Cell Fact. 10, 15.

Miller, G. L. (1959). Use of Dinitrosalicylic Acid Reagent for Determination of Reducing Sugar. Anal. Chem. 31, 426-428.

Naidoo, K., Kumar, A., Sharma, V., Permaul, K., and Singh, S. (2015). Purification and Characterization of an Endoinulinase from *Xanthomonas campestris* pv. *phaseoli* KM 24 Mutant. 53, 146-153.

Onodera, S., and Shiomi, N. (1988). Purification and substrate specificity of endo-type inulinase from *Penicillium purpurogenum*. Agric. Biol. Chem. 52, 2569-2576.

Onodera, S., Murakami, T., Ito, H., Mori, H., Matsui, H., Honma, M., Chiba, S., and Shiomi, N. (1996). Molecular Cloning and Nucleotide Sequences of cDNA and Gene Encoding endo-Inulinase from *Penicillium purpurogenum*. Biosci. Biotechnol. Biochem. 60, 1780-1785.

Wang, P., Ma, J., Zhang, Y., Zhang, M., Wu, M., Dai, Z., and Jiang, M. (2016). Efficient Secretory Overexpression of Endoinulinase in *Escherichia coli* and the Production of Inulooligosaccharides. Appl. Biochem. Biotechnol. 179, 880-894

Xu, Y., Zheng, Z., Xu, Q., Yong, Q., and Ouyang, J. (2016). Efficient Conversion of Inulin to Inulooligosaccharides through Endoinulinase from *Aspergillus niger*. J. Agric. Food Chem. 64, 2612-2618.

Zelena, K., Eisele, N., and Berger, R. G. (2014). *Escherichia coli* as a production host for novel enzymes from basidiomycota. Biotechnol. Adv. 32, 1382-1395.

The invention claimed is:

1. A modified endoinulinase being a modified wild-type *T. purpuregenus* endoinulinase comprising an amino acid sequence set forth in SEQ ID NO: 1 with a substitution of tyrosine at position 128 (Y128) to H, K, or R or a functional fragment thereof both comprising an amino acid sequence having at least 90% identity to a *T. purpuregenus* wild-type sequence of endoinulinase set forth in SEQ ID NO: 3, wherein any one of said modified endoinulinase or said functional fragment thereof optionally further comprises one or more amino acid substitutions in positions corresponding to position 316, 344, 350 or 504 of said wild-type *T. purpuregenus* endoinulinase.

2. The modified endoinulinase or a functional fragment thereof of claim 1, wherein any one of:
   (i) the tyrosine residue corresponding to Y128 is substituted with H (Y128H);
   (ii) a glutamate residue corresponding to E344 is substituted with K, H or R;
   (iii) a threonine residue corresponding to T504 is substituted with M, S, or Y;
   (iv) an alanine residue corresponding to A316 is substituted with T, S, C, or M; and
   (v) a glutamine residue corresponding to Q350 is substituted with L, G, A, V, or I.

3. The modified endoinulinase or a functional fragment thereof of claim 2, wherein the tyrosine residue corresponding to Y128 is substituted with H; the glutamate residue corresponding to E344 is substituted with K; the threonine residue corresponding to T504 is substituted with M; and the alanine residue corresponding to A316 is substituted with T.

4. The modified endoinulinase or a functional fragment thereof of claim 2, devoid of a 25 amino acid long signal peptide of the wild-type *T. purpureogenus* endoinulinase (SEQ ID NO: 1).

5. The modified endoinulinase or a functional fragment thereof of claim 2 being devoid of any other modifications compared to the *T. purpuregenus* wild-type endoinulinase (SEQ ID NO: 3).

6. An isolated nucleic acid molecule comprising a nucleic acid sequence encoding the modified endoinulinase or a functional fragment thereof, of claim 1.

7. The isolated nucleic acid molecule of claim 6, being optimized for expression in *E. coli* bacteria.

8. The isolated nucleic acid molecule of claim 6 comprising a nucleic acid sequence selected from the group consisting of: SEQ ID NO: 5, SEQ ID NO: 6, SEQ ID NO: 7, and SEQ ID NO: 8.

9. An isolated nucleic acid molecule comprising a nucleic acid sequence codon-optimized for expression in *E. coli* bacteria, wherein said nucleic acid sequence is set forth in SEQ ID NO: 2 and is encoding *T. purpuregenus* wild-type endoinulinase.

10. An expression vector comprising the isolated nucleic acid molecule of claim 6, being operably linked to a promoter.

11. A cell comprising:
   (i) the isolated nucleic acid molecule of claim 6;
   (ii) an isolated nucleic acid molecule comprising a nucleic acid sequence codon-optimized for expression in *E. coli* bacteria, wherein said nucleic acid sequence is set forth in SEQ ID NO: 2 and is encoding *T. purpuregenus* wild-type endoinulinase; or
   (iii) an expression vector comprising the isolated nucleic acid molecule of (i) or (ii).

12. The cell of claim 11, being a bacterial cell.

13. A method for producing a modified endoinulinase, or a functional fragment thereof, comprising: (i) cultivating the cell of claim 11; and (ii) separating said modified endoinulinase from said cell, thereby obtaining a modified endoinulinase.

14. The method of claim 13, wherein said cell is a bacterial cell.

15. The method of claim 13, wherein more than 50% of an activity of said modified endoinulinase or a functional fragment thereof, is in a soluble fraction, and its functional activity is about five-fold higher, as compared with unmodified endoinulinase.

16. The method of claim 13, wherein said modified endoinulinase is *T. purpuregenus* endoinulinase comprising Y128H, and optionally further comprising:
   (i) E344K and T504M;
   (ii) E344K, T504M and Q350L; or
   (iii) E344K, T504M and A316T.

17. The method of claim 13, in which the modified endoinulinase- or a functional fragment thereof, has an amino acid sequence which is at least 95% identical to the sequence of unmodified *T. purpuregenus* wild-type endoinulinase (SEQ ID NO: 3).

18. The method of claim 16, wherein the amino acid sequence is devoid of any other modification compared to the *T. purpuregenus* wild-type endoinulinase (SEQ ID NO: 3).

19. A method for producing fructooligosaccharides, comprising contacting inulin with the modified endoinulinase, or a functional fragment thereof, of claim 1.

20. The modified endoinulinase or a functional fragment thereof of claim 2, wherein:
   (i) a glutamate residue corresponding to E344 is substituted with K; a threonine residue corresponding to T504 is substituted with M; and optionally an alanine residue corresponding to A316 is substituted with T; or
   (ii) a glutamate residue corresponding to E344 is substituted with K; a threonine residue corresponding to T504 is substituted with M; and a glutamine residue corresponding to Q350 is substituted with L.

* * * * *

SEQUENCE LISTING

```
<160> NUMBER OF SEQ ID NOS: 8

<210> SEQ ID NO 1
<211> LENGTH: 515
<212> TYPE: PRT
<213> ORGANISM: Talaromyces purpureogenus

<400> SEQUENCE: 1

Met Ile Ser Leu Arg Ile Ala Leu Ala Ile Asn Ala Leu Ser Tyr Ile
1               5                   10                  15

Cys Ala Leu Val Glu Leu Ala Val Ala Asp Asp Tyr Arg Pro Thr Phe
            20                  25                  30

His Phe Cys Pro Ala Glu Asn Trp Met Asn Glu Pro Asn Gly Leu Ile
        35                  40                  45

Lys Ile Asp Ser Thr Trp His Leu Phe Tyr Gln Ala Asp Pro Thr Ala
    50                  55                  60

Asn Val Trp Gly Asn Glu Cys Trp Gly His Ala Thr Ser Ser Asp Leu
65                  70                  75                  80

Leu His Trp Asp His Leu Pro Val Ala Ile Pro Val Glu Asn Gly Ile
                85                  90                  95

Glu Ser Phe Thr Gly Thr Ser Tyr Tyr Asp Ala Asn Asn Thr Ser Ser
            100                 105                 110

Leu Gly Thr Ser Thr Asn Pro Pro Tyr Leu Ala Phe Phe Thr Gly Tyr
        115                 120                 125

Thr Ser Ser Asn Gly Thr Gln Asp Gln Arg Leu Ala Tyr Ser Thr Asp
    130                 135                 140
```

Leu Gly Thr Thr Trp Leu Lys Phe Ser Gly Asn Pro Ile Ile Ser Ala
145                 150                 155                 160

Ala Leu Glu Ala Pro His Asp Val Thr Gly Leu Glu Ser Arg Asp
            165                 170                 175

Pro Lys Val Phe Phe His Glu Pro Ser Gly Lys Trp Val Met Val Leu
            180                 185                 190

Ala His Gly Gly Gln Asp Lys Leu Thr Phe Trp Thr Ser Leu Asp Ala
            195                 200                 205

Lys Ser Trp Thr Trp Met Ser Asp Leu Leu Ala Ser Gln Ile Glu Gly
            210                 215                 220

Phe Pro Ser Ser Val Thr Gly Trp Glu Val Pro Asp Met Phe Gln Leu
225                 230                 235                 240

Pro Ile Gln Gly Thr Asn Glu Thr Thr Trp Val Ile Ile Phe Thr Pro
                245                 250                 255

Ala Gln Gly Ser Pro Ala Gly Gly Asn Gly Val Val Ala Leu Thr Gly
            260                 265                 270

Ser Phe Asp Gly Glu Thr Phe Leu Ala Asn Pro Val Asp Ser Ser Thr
            275                 280                 285

Leu Trp Leu Asp Tyr Gly Arg Asp Phe Asp Gly Ala Met Ser Trp Glu
290                 295                 300

Asn Val Pro Ala Ser Asp Gly Arg Leu Ile Ile Ala Ala Val Met Asn
305                 310                 315                 320

Ser Tyr Gly Ser Asn Pro Pro Thr Asn Thr Trp Lys Gly Met Leu Ser
                325                 330                 335

Phe Pro Arg Thr Leu Thr Leu Glu Lys Ile Gly Ser Lys Gln Tyr Phe
            340                 345                 350

Leu Gln Gln Pro Ile Ala Glu Leu Ser Thr Val Asp Asn Ala Leu Ala
            355                 360                 365

Ser Ile Gln Asn Gln Thr Ile Ala Pro Lys Gly Thr Leu Leu Ser Ser
370                 375                 380

Ile His Gly Ser Ser Leu Asp Val Arg Ile Ala Phe Ser Val Asp Ser
385                 390                 395                 400

Gly Ala Thr Leu Ser Leu Ala Val Arg Lys Gly Gly Ser Glu Gln Thr
            405                 410                 415

Val Ile Arg Tyr Ser Gln Ser Asn Ser Thr Leu Ser Val Asp Arg Thr
            420                 425                 430

Ala Ser Gly Asp Ile Ser Tyr Asp Pro Ala Ala Gly Gly Ile His Ser
            435                 440                 445

Ala Gln Leu Ala Arg Asp Asn Thr Glu Leu Val Tyr Leu Arg Val Leu
            450                 455                 460

Val Asp Thr Cys Ser Val Glu Val Phe Gly Gly Gln Gly Glu Ala Val
465                 470                 475                 480

Ile Ser Asp Leu Ile Phe Pro Ser Asn Ser Ser Asp Gly Leu Ser Leu
                485                 490                 495

Glu Val Ile Gly Gly Thr Ala Thr Leu Gln Ser Val Glu Val Phe Ser
                500                 505                 510

Val Ser Leu
        515

<210> SEQ ID NO 2
<211> LENGTH: 1476
<212> TYPE: DNA
<213> ORGANISM: Artificial Sequence
<220> FEATURE:

<223> OTHER INFORMATION: Synthetic sequence

<400> SEQUENCE: 2

```
atggacgact atcgcccgac cttcatttc tgcccggcgg aaaactggat gaatgaaccg      60
aacggcctga ttaaaatcga cagcacctgg cacctgtttt atcaggcaga tccgacggct     120
aatgtgtggg gcaacgaatg ttggggtcac gcaaccagct ctgatctgct gcattgggac     180
cacctgccgg ttgctattcc ggtcgaaaat ggcatcgaat ccttcaccgg tacgtcatat     240
tacgatgcga acaataccag ttccctgggc accagcacga atccgccgta tctggccttt     300
ttcaccggct acacgtcatc gaacggcacc caggatcaac gtctggccta tagcacggac     360
ctgggcacca cgtggctgaa attttccggt aacccgatta tctcagcggc cctggaagca     420
ccgcacgatg tgaccggcgg tctggaatct cgcgacccga agtgtttttt ccatgaaccg     480
agtggcaaat gggtcatggt gctggcgcac ggcggtcagg ataaactgac cttctggacg     540
tcgctggacg caaaaagctg gacctggatg tctgatctgc tggctagtca aattgaaggc     600
tttccgagct ctgtgaccgg ttgggaagtt ccggatatgt ccagctgcc gatccaaggc      660
accaatgaaa ccacgtgggt gattatcttt acgccggcac agggctctcc ggccggcggt     720
aatggtgtgg ttgcgctgac cggcagtttt gatggtgaaa cgttcctggc caacccggtt     780
gatagttcca ccctgtggct ggactatggc cgtgatttcg acggtgcgat gtcttgggaa     840
aatgtcccgg ccagtgatgg ccgcctgatt atcgcagctg tgatgaactc ctacggctca     900
aatccgccga ccaacacgtg gaagggtatg ctgtcctttc gcgtaccct gacgctggaa      960
aaaattggtt caaacagta tttcctgcag caaccgatcg cagaactgtc caccgtggat     1020
aatgcactgg cttcaattca gaaccaaacc atcgctccga acagacgct gctgtcatcg     1080
attcatggca gctctctgga tgtccgtatc gcatttcgg tggacagcgg tgcaaccctg     1140
tcgctggctg ttcgtaaagg cggtagcgaa cagacggtca ttcgctattc acaatcgaat     1200
agcaccctga gcgttgatcg cacggcctct ggcgatatta gttacgaccc ggcagccggc     1260
ggtatccaca gcgcgcagct ggcccgtgac aacaccgaac tggtgtatct gcgcgttctg     1320
gtcgatacgt gcagtgtgga agtttttggc ggtcaaggcg aagcggttat ttcggacctg     1380
atcttcccga gcaacagttc cgatggtctg tcgctggaag ttattggcgg caccgcaacg     1440
ctgcagtccg tcgaagtgtt ttctgtcagt ctgtga                              1476
```

<210> SEQ ID NO 3
<211> LENGTH: 491
<212> TYPE: PRT
<213> ORGANISM: Artificial Sequence
<220> FEATURE:
<223> OTHER INFORMATION: Synthetic sequence

<400> SEQUENCE: 3

```
Met Asp Asp Tyr Arg Pro Thr Phe His Phe Cys Pro Ala Glu Asn Trp
1               5                   10                  15

Met Asn Glu Pro Asn Gly Leu Ile Lys Ile Asp Ser Thr Trp His Leu
            20                  25                  30

Phe Tyr Gln Ala Asp Pro Thr Ala Asn Val Trp Gly Asn Glu Cys Trp
        35                  40                  45

Gly His Ala Thr Ser Ser Asp Leu Leu His Trp Asp His Leu Pro Val
    50                  55                  60

Ala Ile Pro Val Glu Asn Gly Ile Glu Ser Phe Thr Gly Thr Ser Tyr
65                  70                  75                  80
```

```
Tyr Asp Ala Asn Asn Thr Ser Ser Leu Gly Thr Ser Thr Asn Pro Pro
                85                  90                  95

Tyr Leu Ala Phe Phe Thr Gly Tyr Thr Ser Ser Asn Gly Thr Gln Asp
            100                 105                 110

Gln Arg Leu Ala Tyr Ser Thr Asp Leu Gly Thr Thr Trp Leu Lys Phe
        115                 120                 125

Ser Gly Asn Pro Ile Ile Ser Ala Ala Leu Glu Ala Pro His Asp Val
    130                 135                 140

Thr Gly Gly Leu Glu Ser Arg Asp Pro Lys Val Phe Phe His Glu Pro
145                 150                 155                 160

Ser Gly Lys Trp Val Met Val Leu Ala His Gly Gly Gln Asp Lys Leu
                165                 170                 175

Thr Phe Trp Thr Ser Leu Asp Ala Lys Ser Trp Thr Trp Met Ser Asp
            180                 185                 190

Leu Leu Ala Ser Gln Ile Glu Gly Phe Pro Ser Ser Val Thr Gly Trp
        195                 200                 205

Glu Val Pro Asp Met Phe Gln Leu Pro Ile Gln Gly Thr Asn Glu Thr
    210                 215                 220

Thr Trp Val Ile Ile Phe Thr Pro Ala Gln Gly Ser Pro Ala Gly Gly
225                 230                 235                 240

Asn Gly Val Val Ala Leu Thr Gly Ser Phe Asp Gly Glu Thr Phe Leu
                245                 250                 255

Ala Asn Pro Val Asp Ser Ser Thr Leu Trp Leu Asp Tyr Gly Arg Asp
            260                 265                 270

Phe Asp Gly Ala Met Ser Trp Glu Asn Val Pro Ala Ser Asp Gly Arg
        275                 280                 285

Leu Ile Ile Ala Ala Val Met Asn Ser Tyr Gly Ser Asn Pro Pro Thr
    290                 295                 300

Asn Thr Trp Lys Gly Met Leu Ser Phe Pro Arg Thr Leu Thr Leu Glu
305                 310                 315                 320

Lys Ile Gly Ser Lys Gln Tyr Phe Leu Gln Gln Pro Ile Ala Glu Leu
                325                 330                 335

Ser Thr Val Asp Asn Ala Leu Ala Ser Ile Gln Asn Gln Thr Ile Ala
            340                 345                 350

Pro Lys Gln Thr Leu Leu Ser Ser Ile His Gly Ser Ser Leu Asp Val
        355                 360                 365

Arg Ile Ala Phe Ser Val Asp Ser Gly Ala Thr Leu Ser Leu Ala Val
    370                 375                 380

Arg Lys Gly Gly Ser Glu Gln Thr Val Ile Arg Tyr Ser Gln Ser Asn
385                 390                 395                 400

Ser Thr Leu Ser Val Asp Arg Thr Ala Ser Gly Asp Ile Ser Tyr Asp
                405                 410                 415

Pro Ala Ala Gly Gly Ile His Ser Ala Gln Leu Ala Arg Asp Asn Thr
            420                 425                 430

Glu Leu Val Tyr Leu Arg Val Leu Val Asp Thr Cys Ser Val Glu Val
        435                 440                 445

Phe Gly Gly Gln Gly Glu Ala Val Ile Ser Asp Leu Ile Phe Pro Ser
    450                 455                 460

Asn Ser Ser Asp Gly Leu Ser Leu Glu Val Ile Gly Gly Thr Ala Thr
465                 470                 475                 480

Leu Gln Ser Val Glu Val Phe Ser Val Ser Leu
                485                 490
```

<210> SEQ ID NO 4
<211> LENGTH: 1170
<212> TYPE: DNA
<213> ORGANISM: Artificial Sequence
<220> FEATURE:
<223> OTHER INFORMATION: Synthetic sequence

<400> SEQUENCE: 4

| | | | | | |
|---|---|---|---|---|---|
| atgcaccatc | accatcacca | ttccggcaaa | actgaagaag | gtaaactggt | aatctggatt | 60 |
| aacggcgata | aaggctataa | cggtctcgct | gaagtcggta | agaaattcga | gaaagatacc | 120 |
| ggaattaaag | tcaccgttga | gcatccggat | aaactggaag | agaaattccc | acaggttgcg | 180 |
| gcaactggcg | atgccctga | cattatcttc | tgggcacacg | accgctttgg | tggctacgct | 240 |
| caatctggcc | tgttggctga | atcaccccg | gacaaagcgt | tccaggacaa | gctgtatccg | 300 |
| tttacctggg | atgccgtacg | ttacaacggc | aagctgattg | cttacccgat | cgctgttgaa | 360 |
| gcgttatcgc | tgatttataa | caaagatctg | ctgccgaacc | cgccaaaaac | ctgggaagag | 420 |
| atcccggcgc | tggataaaga | actgaaagcg | aaggtaaga | gcgcgctgat | gttcaacctg | 480 |
| caagaaccgt | acttcacctg | gccgctgatt | gctgctgacg | ggggttatgc | gttcaagtat | 540 |
| gaaaacggca | gtacgacat | taagacgtg | ggcgtggata | cgctggcgc | gaaagcgggt | 600 |
| ctgaccttcc | tggttgacct | gattaaaaac | aaacacatga | atgcagacac | cgattactcc | 660 |
| atcgcagaag | ctgcctttaa | taaaggcgaa | acagcgatga | ccatcaacgg | cccgtgggca | 720 |
| tggtccaaca | tcgacaccag | caaagtgaat | tatggtgtaa | cggtactgcc | gaccttcaag | 780 |
| ggtcaaccat | ccaaaccgtt | cgttggcgtg | ctgagcgcag | gtattaacgc | cgccagtccg | 840 |
| aacaaagagc | tggcgaaaga | gttcctcgaa | aactatctgc | tgactgatga | aggtctggaa | 900 |
| gcggttaata | aagacaaacc | gctgggtgcc | gtagcgctga | gtcttacga | ggaagagttg | 960 |
| gcgaaagatc | cacgtattgc | cgccactatg | gaaaacgccc | agaaaggtga | aatcatgccg | 1020 |
| aacatcccgc | agatgtccgc | tttctggtat | gccgtgcgta | ctgcggtgat | caacgccgcc | 1080 |
| agcggtcgtc | agactgtcga | tgaagccctg | aaagacgcg | agactaattc | gagctcggta | 1140 |
| ccgtcctctc | tcgtgatcga | gggtaggcct | | | | 1170 |

<210> SEQ ID NO 5
<211> LENGTH: 1476
<212> TYPE: DNA
<213> ORGANISM: Artificial Sequence
<220> FEATURE:
<223> OTHER INFORMATION: Synthetic sequence

<400> SEQUENCE: 5

| | | | | | |
|---|---|---|---|---|---|
| atggacgact | atcgcccgac | ctttcatttc | tgcccggcgg | aaaactggat | gaatgaaccg | 60 |
| aacggcctga | ttaaaatcga | cagcacctgg | cacctgtttt | atcaggcaga | tccgacgggt | 120 |
| aatgtgtggg | gcaacgaatg | ttggggtcac | gcaaccagct | ctgatctgct | gcattgggac | 180 |
| cacctgccgg | ttgctattcc | ggtcgaaaat | ggcatcgaat | ccttcaccgg | tacgtcatat | 240 |
| tacgatgcga | acaataccag | ttccctgggc | accagcacga | atccgccgta | tctggccttt | 300 |
| ttcaccggcc | acacgtcatc | gaacggcacc | caggatcaac | gtctggccta | tagcacggac | 360 |
| ctgggcacca | cgtggctgaa | attttccggt | aacccgatta | tctcagcggc | cctggaagca | 420 |
| ccgcacgatg | tgaccggcgg | tctggaatct | cgcgacccga | agtgtttttt | ccatgaaccg | 480 |
| agtggcaaat | gggtcatggt | gctggcgcac | ggcggtcagg | ataaactgac | cttctggacg | 540 |
| tcgctggacg | caaaaagctg | gacctggatg | tctgatctgc | tggctagtca | aattgaaggc | 600 |

| | |
|---|---|
| tttccgagct ctgtgaccgg ttgggaagtt ccggatatgt tccagctgcc gatccaaggc | 660 |
| accaatgaaa ccacgtgggt gattatcttt acgccggcac agggctctcc ggccggcggt | 720 |
| aatggtgtgg ttgcgctgac cggcagtttt gatggtgaaa cgttcctggc caacccggtt | 780 |
| gatagttcca ccctgtggct ggactatggc cgtgatttcg acggtgcgat gtcttgggaa | 840 |
| aatgtcccgg ccagtgatgg ccgcctgatt atcgcagctg tgatgaactc ctacggctca | 900 |
| aatccgccga ccaacacgtg aagggtatg ctgtcctttc cgcgtaccct gacgctggaa | 960 |
| aaaattggtt caaaacagta tttcctgcag caaccgatcg cagaactgtc caccgtggat | 1020 |
| aatgcactgg cttcaattca gaaccaaacc atcgctccga acagacgct gctgtcatcg | 1080 |
| attcatggca gctctctgga tgtccgtatc gcattttcgg tggacagcgg tgcaaccctg | 1140 |
| tcgctggctg ttcgtaaagg cggtagcgaa cagacggtca ttcgctattc acaatcgaat | 1200 |
| agcaccctga gcgttgatcg cacggcctct ggcgatatta gttacgaccc ggcagccggc | 1260 |
| ggtatccaca gcgcgcagct ggcccgtgac aacaccgaac tggtgtatct gcgcgttctg | 1320 |
| gtcgatacgt gcagtgtgga agttttggc ggtcaaggcg aagcggttat ttcggacctg | 1380 |
| atcttcccga gcaacagttc cgatggtctg tcgctggaag ttattggcgg caccgcaacg | 1440 |
| ctgcagtccg tcgaagtgtt ttctgtcagt ctgtga | 1476 |

<210> SEQ ID NO 6
<211> LENGTH: 1476
<212> TYPE: DNA
<213> ORGANISM: Artificial Sequence
<220> FEATURE:
<223> OTHER INFORMATION: Synthetic sequence

<400> SEQUENCE: 6

| | |
|---|---|
| atggacgact atcgcccgac ctttcatttc tgcccggcgg aaaactggat gaatgaaccg | 60 |
| aacggcctga ttaaaatcga cagcacctgg cacctgtttt atcaggcaga tccgacggct | 120 |
| aatgtgtggg gcaacgaatg ttgggtcac gcaaccagct ctgatctgct gcattgggac | 180 |
| cacctgccgg ttgctattcc ggtcgaaaat ggcatcgaat ccttcaccgg tacgtcatat | 240 |
| tacgatgcga caataccag ttccctgggc accagcacga atccgccgta tctggccttt | 300 |
| ttcaccggcc acacgtcatc gaacggcacc caggatcaac gtctggccta tagcacggac | 360 |
| ctgggcacca cgtggctgaa attttccggt aacccgatta tctcagcggc cctggaagca | 420 |
| ccgcacgatg tgaccggcgg tctggaatct cgcgacccga agtgttttt ccatgaaccg | 480 |
| agtggcaaat gggtcatggt gctggcgcac ggcggtcagg ataaactgac cttctggacg | 540 |
| tcgctggacg caaaaagctg gacctggatg tctgatctgc tggctagtca aattgaaggc | 600 |
| tttccgagct ctgtgaccgg ttgggaagtt ccggatatgt tccagctgcc gatccaaggc | 660 |
| accaatgaaa ccacgtgggt gattatcttt acgccggcac agggctctcc ggccggcggt | 720 |
| aatggtgtgg ttgcgctgac cggcagtttt gatggtgaaa cgttcctggc caacccggtt | 780 |
| gatagttcca ccctgtggct ggactatggc cgtgatttcg acggtgcgat gtcttgggaa | 840 |
| aatgtcccgg ccagtgatgg ccgcctgatt atcgcagctg tgatgaactc ctacggctca | 900 |
| aatccgccga ccaacacgtg aagggtatg ctgtcctttc cgcgtaccct gacgctgaaa | 960 |
| aaaattggtt caaaacagta tttcctgcag caaccgatcg cagaactgtc caccgtggat | 1020 |
| aatgcactgg cttcaattca gaaccaaacc atcgctccga acagacgct gctgtcatcg | 1080 |
| attcatggca gctctctgga tgtccgtatc gcattttcgg tggacagcgg tgcaaccctg | 1140 |
| tcgctggctg ttcgtaaagg cggtagcgaa cagacggtca ttcgctattc acaatcgaat | 1200 |

| agcaccctga gcgttgatcg cacggcctct ggcgatatta gttacgaccc ggcagccggc | 1260 |
| ggtatccaca gcgcgcagct ggcccgtgac aacaccgaac tggtgtatct gcgcgttctg | 1320 |
| gtcgatacgt gcagtgtgga agtttttggc ggtcaaggcg aagcggttat ttcggacctg | 1380 |
| atcttcccga gcaacagttc cgatggtctg tcgctggaag ttattggcgg caccgcaatg | 1440 |
| ctgcagtccg tcgaagtgtt ttctgtcagt ctgtga | 1476 |

<210> SEQ ID NO 7
<211> LENGTH: 1476
<212> TYPE: DNA
<213> ORGANISM: Artificial Sequence
<220> FEATURE:
<223> OTHER INFORMATION: Synthetic sequence

<400> SEQUENCE: 7

| atggacgact atcgcccgac ctttcatttc tgcccggcgg aaaactggat gaatgaaccg | 60 |
| aacggcctga ttaaaatcga cagcaccctg cacctgtttt atcaggcaga tccgacggct | 120 |
| aatgtgtggg gcaacgaatg ttggggtcac gcaaccagct ctgatctgct gcattgggac | 180 |
| cacctgccga ttgctattcc ggtcgaaaat ggcatcgaat ccttcaccgg tacgtcatat | 240 |
| tacgatgcga acaataccag ttccctgggc accagcacga atccgccgta tctggccttt | 300 |
| ttcaccggcc acacgtcatc gaacggcacc caggatcaac gtctggccta tagcacggac | 360 |
| ctgggcacca cgtggctgaa attttccggt aacccgatta tctcagcggc cctggaagca | 420 |
| ccgcacgatg tgaccggcgg tctggaatct cgcgacccga agtgtttttt ccatgaaccg | 480 |
| agtggcaaat gggtcatggt gctggcgcac ggcggtcagg ataaactgac cttctggacg | 540 |
| tcgctggacg caaaaagctg gacctggatg tctgatctgc tggctagtca aattgaaggc | 600 |
| tttccgagct ctgtgaccgg ttgggaagtt ccggatatgt ccagctgcc gatccaaggc | 660 |
| accaatgaaa ccacgtgggt gattatcttt acgccggcac agggctctcc ggccggcggt | 720 |
| aatggtgtgg ttgcgctgac cggcagtttt gatggtgaaa cgttcctggc caacccggtt | 780 |
| gatagttcca ccctgtggct ggactatggc cgtgatttcg acggtgcgat gtcttgggaa | 840 |
| aatgtcccgg ccagtgatgg ccgcctgatt atcgcagctg tgatgaactc ctacggctca | 900 |
| aatccgccga ccaacacgtg gaagggtatg ctgtcctttc gcgtaccct gacgctgaaa | 960 |
| aaaattggtt caaaactgta tttcctgcag caaccgatcg cagaactgtc caccgtggat | 1020 |
| aatgcactgg cttcaattca gaaccaaacc atcgctccga acagacgct gctgtcatcg | 1080 |
| attcatggca gctctctgga tgtccgtatc gcattttcgg tggacagcgg tgcaaccctg | 1140 |
| tcgctggctg ttcgtaaagg cggtagcgaa cagacggtca ttcgctattc acaatcgaat | 1200 |
| agcaccctga gcgttgatcg cacggcctct ggcgatatta gttacgaccc ggcagccggc | 1260 |
| ggtatccaca gcgcgcagct ggcccgtgac aacaccgaac tggtgtatct gcgcgttctg | 1320 |
| gtcgatacgt gcagtgtgga agtttttggc ggtcaaggcg aagcggttat ttcggacctg | 1380 |
| atcttcccga gcaacagttc cgatggtctg tcgctggaag ttattggcgg caccgcaatg | 1440 |
| ctgcagtccg tcgaagtgtt ttctgtcagt ctgtga | 1476 |

<210> SEQ ID NO 8
<211> LENGTH: 1476
<212> TYPE: DNA
<213> ORGANISM: Artificial Sequence
<220> FEATURE:
<223> OTHER INFORMATION: Synthetic sequence

```
<400> SEQUENCE: 8
atggacgact atcgcccgac ctttcatttc tgcccggcgg aaaactggat gaatgaaccg      60
aacggcctga ttaaaatcga cagcacctgg cacctgtttt atcaggcaga tccgacggct     120
aatgtgtggg gcaacgaatg ttggggtcac gcaaccagct ctgatctgct gcattgggac     180
cacctgccgg ttgctattcc ggtcgaaaat ggcatcgaat ccttcaccgg tacgtcatat     240
tacgatgcga acaataccag ttccctgggc accagcacga atccgccgta tctggccttt     300
ttcaccggcc acacgtcatc gaacggcacc caggatcaac gtctggccta tagcacggac     360
ctgggcacca cgtggctgaa attttccggt aacccgatta tctcagcggc cctggaagca     420
ccgcacgatg tgaccggcgg tctggaatct cgcgacccga aagtgttttt ccatgaaccg     480
agtggcaaat gggtcatggt gctggcgcac ggcggtcagg ataaactgac cttctggacg     540
tcgctggacg caaaaagctg gacctggatg tctgatctgc tggctagtca aattgaaggc     600
tttccgagct ctgtgaccgg ttgggaagtt ccggatatgt tccagctgcc gatccaaggc     660
accaatgaaa ccacgtgggt gattatcttt acgccggcac agggctctcc ggccggcggt     720
aatggtgtgg ttgcgctgac cggcagtttt gatggtgaaa cgttcctggc caacccggtt     780
gatagttcca ccctgtggct ggactatggc cgtgatttcg acggtgcgat gtcttgggaa     840
aatgtcccgg ccagtgatgg ccgcctgatt atcacagctg tgatgaactc ctacggctca     900
aatccgccga ccaacacgtg gaagggtatg ctgtcctttc cgcgtaccct gacgctgaaa     960
aaaattggtt caaaacagta tttcctgcag caaccgatcg cagaactgtc caccgtggat    1020
aatgcactgg cttcaattca gaaccaaacc atcgctccga aacagacgct gctgtcatcg    1080
attcatggca gctctctgga tgtccgtatc gcattttcgg tggacagcgg tgcaaccctg    1140
tcgctggctg ttcgtaaagg cggtagcgaa cagacggtca ttcgctattc acaatcgaat    1200
agcaccctga gcgttgatcg cacggcctct ggcgatatta gttacgaccc ggcagccggc    1260
ggtatccaca gcgcgcagct ggcccgtgac aacaccgaac tggtgtatct gcgcgttctg    1320
gtcgatacgt gcagtgtgga agttttttggc ggtcaaggcg aagcggttat ttcggacctg    1380
atcttcccga gcaacagttc cgatggtctg tcgctggaag ttattggcgg caccgcaatg    1440
ctgcagtccg tcgaagtgtt ttctgtcagt ctgtga                              1476
```